US012560599B2

(12) United States Patent
Kostovic et al.

(10) Patent No.: US 12,560,599 B2
(45) Date of Patent: *Feb. 24, 2026

(54) SAMPLE CLARIFICATION AND REDUCTION OF BACKGROUND FLUORESCENCE FOR FLUORESCENT DETECTION OF ANALYTES

(71) Applicant: Ellie LLC, Germantown, WI (US)

(72) Inventors: Miladin Kostovic, Brookfield, WI (US); Milovan Stojanovic, Vrnjacka Banja (RS)

(73) Assignee: Ellie LLC, Germantown, WI (US)

( * ) Notice: Subject to any disclaimer, the term of this patent is extended or adjusted under 35 U.S.C. 154(b) by 821 days.

This patent is subject to a terminal disclaimer.

(21) Appl. No.: 17/869,160

(22) Filed: Jul. 20, 2022

(65) Prior Publication Data

US 2022/0365081 A1 Nov. 17, 2022

Related U.S. Application Data

(63) Continuation of application No. 16/389,457, filed on Apr. 19, 2019, now Pat. No. 11,435,342.

(60) Provisional application No. 62/659,946, filed on Apr. 19, 2018.

(51) Int. Cl.
*G01N 33/543* (2006.01)
*G01N 33/542* (2006.01)

(52) U.S. Cl.
CPC ..... *G01N 33/54366* (2013.01); *G01N 33/542* (2013.01); *G01N 33/54333* (2013.01)

(58) Field of Classification Search
None
See application file for complete search history.

(56) References Cited

U.S. PATENT DOCUMENTS

| | | | |
|---|---|---|---|
| 4,140,806 A | 2/1979 | Glimenius | |
| 4,439,432 A | 3/1984 | Peat | |
| 4,587,212 A | 5/1986 | Baker | |
| 5,101,015 A | 3/1992 | Brynes et al. | |
| 5,239,086 A | 8/1993 | Dubler et al. | |
| 5,262,333 A | 11/1993 | Heiman | |
| 5,264,373 A | 11/1993 | Wang et al. | |

(Continued)

FOREIGN PATENT DOCUMENTS

EP 0371253 6/1990

OTHER PUBLICATIONS

International Search Report issued for PCT/US2019/028322, dated Jun. 21, 2019.

(Continued)

*Primary Examiner* — Rebecca M Giere
(74) *Attorney, Agent, or Firm* — Daniel A. Blasiole; DeWitt LLP

(57) ABSTRACT

Methods and reagents for processing samples for fluorescence analysis. Processing methods include treating samples containing riboflavin to reduce riboflavin-dependent autofluorescence by adding riboflavin binding protein to the sample, irradiating the sample, or a combination thereof. Processing methods also include clarifying samples by coagulating, precipitating, and/or otherwise removing proteins and other components that interfere with fluorescence analysis without removing the analyte. Fluorescence analysis methods include fluorescence polarization analysis (FPA) and others. Reagents suitable for performing the disclosed methods are provided.

20 Claims, 7 Drawing Sheets

Absorbed Polarized Light + Fluorophore orientation at absorption nsec Molecular Motion Fluorophore orientation at emission + Emitted Depolarized Light

(56) References Cited

U.S. PATENT DOCUMENTS

| | | | |
|---|---|---|---|
| 5,273,765 | A | 12/1993 | Weber |
| 6,812,036 | B2 | 11/2004 | Nasir et al. |
| 2003/0073073 | A1 | 4/2003 | Wolde-Mariam |
| 2010/0121037 | A1 | 5/2010 | Lachkar et al. |

OTHER PUBLICATIONS

International Preliminary Oct. 20, 2020.

Comin et al., Technical Note: Direct Enzyme Immunoassay of Progesterone in Bovine Milk Whey, J. Dairy Sci., vol. 88, pp. 4239-4242.

Dallal et al., Identification and extraction of chicken egg yolk immunoglobulin from egg by polyethylene glycol (PEG) precipitation, J Med Bacteriol. vol. 4, No. 5, 6 (2015): pp. 13-18.

David B. Hand, Determination of Riboflavin in milk, Jun. 15, 1939, Industrial and Engineering Chemistry, vol. 11, No. 6, pp. 306-309.

Gall et al., Fluorescence polarization assay for detection of Brucella abortus antibodies in bulk tank bovine milk samples, clinical and Diagnostic Laboratory Immunology, American Society for Microbiology, vol. 9, No. 6, Nov. 1, 2002, pp. 1356-1360.

Goldring, Isolation of Chicken Immunoglobulins (IgY) from Egg Yolk, Bambed, vol. 31, No. 3, pp. 185-187, 2003.

Hamazume Y, Mega T, Ikenaka T. Characterization of hen egg white- and yolk-riboflavin binding proteins and amino acid sequence of egg white-riboflavin binding protein. J Biochem. Jun. 1984;95(6):1633-44.

Hong JY, Choi MJ. Development of one-step fluorescence polarization immunoassay for progesterone. Biol Pharm Bull. Oct. 2002;25(10):1258-62.

Lea et al., Fluorescence Polarization Assays in Small Molecule Screening, Expert Opin Drug Discov. Jan. 2011 ; 6(1): 17-32.

Marilyn A. Huestis, Human Cannabinoid Pharmacokinetics, Aug. 2007, Chemistry and Biodiversity, vol. 4, Issue 8, pp. 1770-1804.

McCoy, Milk Coagulants, Cheese & Fromage: Common Culters, Montreal, Aug. 3-6, 2011, pp. 1-28.

Murthy US, Podder SK, Adiga PR. The interaction of riboflavin with a protein isolated from hen's egg white: a spectrofluorimetric study. Biochim Biophys Acta. May 20, 1976;434(1):69-81.

Nielsen K, Gall D, Jolley M, Leishman G, Balsevicius S, Smith P, Nicoletti P, Thomas F. A homogeneous fluorescence polarization assay for detection of antibody to Brucella abortus. J Immunol Methods. Sep. 9, 1996;195(1-2):161-8.

Nielsen K, Gall D. Fluorescence polarization assay for the diagnosis of brucellosis: a review. J Immunoassay Immunochem. 2001;22(3):183-201.

Nielsen K, Lin M, Gall D, Jolley M. Fluorescence polarization immunoassay: detection of antibody to Brucella abortus. Methods. Sep. 2000;22(1):71-6.

Nishikimi M, Kyogoku Y. Flavin-protein interaction in egg white flavoprotein. J Biochem. Jun. 1973;73(6):1233-42.

O'Connell et al., Influence of Ethanol on the rennet-induced coagulation of milk, Journal of Diary Research, Vo. 73, pp. 312-317.

Pauly, D., Chacana, P.A., Calzado, E.G., Brembs, B., Schade, R. IgY Technology: Extraction of Chicken Antibodies from Egg Yolk by Polyethylene Glycol (PEG) Precipitation. J. Vis. Exp. (51), e3084, (2011).

Trapiella-Alfonso et al., Development of a quantum dot-based fluorescent immunoassay for progesterone determination in bovine milk, Biosensors and Bioelectronics, Jun. 1, 2011, vol. 26, pp. 4753-4759.

United States Department of Agriculture Animal and Plant Health Inspection Service, Fluorescence Polarization Assay (FP) Test: Field Trial and Testing Results for Validation of the FP Test in Cattle, Bison, and Swine, retrieved Dec. 20, 2017 from the Internet <URL: https://www.aphis.usda.gov/animal_health/animal_diseases/brucellosis/downloads/fpa-val-rpt.pdf>.

Varriale A, Pennacchio A, Pinto G, Oliviero G, D'Errico S, Majoli A, Scala A, Capo A, Pennacchio A, Di Giovanni S, Staiano M, D'Auria S. A Fluorescence Polarization Assay To Detect Steroid Hormone Traces in Milk. J Agric Food Chem. Oct. 21, 2015;63(41):9159-64.

Vianey del R. Torres-Pelayo et al., Variation in the extraction efficiency of estradiol and progesterone in moist and lyophilized feces of the black howler monkey (Alouatta pigra): alternative methods, Dec. 19, 2011, Frontiers in Physiology, vol. 2, Article 97, pp. 1-9.

Wu et al. XF, Cai ZX, Sun SG, Huang Q, Ren GD, He L, Ma MH. [Investigation of interaction between riboflavin and riboflavin binding protein by fluorescence spectroscopy]. Guang Pu Xue Yu Guang Pu Fen Xi. Mar. 2012;32(3):719-22. [Article in Chinese, abstract only].

Zandomeneghi M, Carbonaro L, Zandomeneghi G. Biochemical fluorometric method for the determination of riboflavin in milk. J Agric Food Chem. Jul. 25, 2007;55(15):5990-4.

FIG. 3
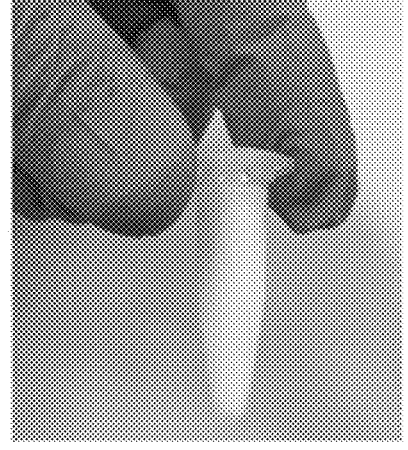
FIG. 4
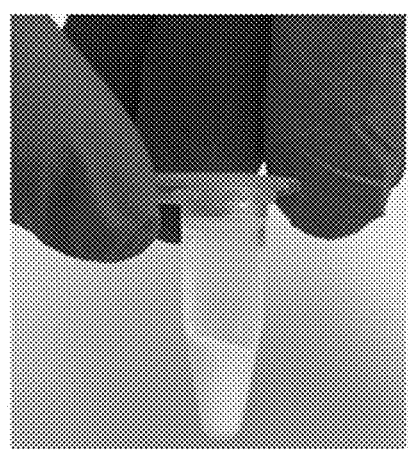
FIG. 5

SAMPLE CLARIFICATION AND REDUCTION OF BACKGROUND FLUORESCENCE FOR FLUORESCENT DETECTION OF ANALYTES

FIELD OF THE INVENTION

The invention is directed to the clarification and/or the reduction of background fluorescence in samples for the fluorescent detection of analytes, such as through the use of fluorescence polarization assay (FPA) or other fluorescence-based assays (FBA).

BACKGROUND

Fluorescence-based assays such as fluorescence polarization assay (FPA) and others are often used to detect analytes in samples. However, fluorescence-based assays are not reliable for certain types of samples such as milk samples, egg yolk samples, and others. These types of samples have a large amount of riboflavin, which causes a high degree of background autofluorescence. The autofluorescence can skew results, making the fluorescence-based assays unreliable. These types of samples also have a large amount of protein and other components that can make the samples opaque to light and thereby resistant to fluorescence analysis. There is a need in the art for methods and reagents for processing samples containing riboflavin and/or other components to make them suitable for fluorescence-based assays.

SUMMARY OF THE INVENTION

One aspect of the invention is directed to methods of treating and testing a sample comprising an analyte. The methods in some versions comprise treating the sample to reduce riboflavin-dependent autofluorescence in the sample, adding a tracer to the sample, and detecting fluorescence from the tracer in the sample. Treating the sample to reduce riboflavin-dependent fluorescence can comprise adding riboflavin binding protein to the sample, irradiating the sample, or a combination thereof. The detecting is preferably performed in the presence of the riboflavin binding protein added to the sample. The detected fluorescence can indicate an amount of analyte in the sample.

Some versions further comprise clarifying the sample. The clarifying is performed in a manner that maintains the analyte in the sample. In some versions, the clarifying comprises coagulating casein in the sample and removing the coagulated casein from the sample. The coagulating can comprise adding a rennet to the sample in an amount sufficient to coagulate the casein. In some versions, the clarifying comprises removing lipid from the sample. The clarifying can comprise centrifuging the sample, filtering the sample, or a combination thereof. The filtering in some versions is conducted with a filter having pore size from about 0.1 μm to about 10 μm.

In preferred versions, the clarifying comprises adding a non-aqueous polar solvent to the sample. The non-aqueous polar solvent can comprise an alcohol. The non-aqueous polar solvent is preferably added to the sample in an amount sufficient to maintain the analyte in the sample, such as during the separation step. The non-aqueous polar solvent in some versions is added to the sample at a final concentration of from about 10% v/v to about 50% v/v. The non-aqueous polar solvent is preferably added to the sample prior to centrifuging and/or filtering the sample.

In some versions, the sample comprises a milk product. The milk product can comprise milk serum.

In some versions, the analyte is a hydrophobic analyte. In some versions, the analyte is progesterone. In some versions, the analyte comprises an antibody or an antigen.

In some versions, the tracer comprises a binding moiety and a fluorescent moiety. The binding moiety can comprise a standard of the analyte or a ligand of the analyte.

In some versions, a ligand to which the analyte and the tracer compete for binding is added to the sample. The ligand is added prior to detecting the fluorescence from the tracer in the sample. In some versions, the detecting comprises detecting plane-polarized light.

The objects and advantages of the invention will appear more fully from the following detailed description of the preferred embodiment of the invention made in conjunction with the accompanying drawings.

BRIEF DESCRIPTION OF THE DRAWINGS

FIG. 3 shows the conversion of pregnenolone to progesterone.

FIG. 4 shows a milk sample before coagulant treatment.

FIG. 5 shows a milk sample after coagulant and centrifuge treatment.

FIG. 6 illustrates the reproductive cycle in Cow #1. The progesterone FPA test showed a drop in progesterone level on day 22. Cow #1 entered estrus on day 25.

FIG. 7 illustrates the reproductive cycle in Cow #2. The progesterone FPA test showed a drop in progesterone level on day 19. Cow #2 entered estrus on day 21.

FIG. 8 illustrates the reproductive cycle in Cow #3. The progesterone FPA test showed a high progesterone level during the whole experiment with a conclusion of possible pregnancy.

FIG. 9 illustrates the reproductive cycle in Cow #4. The progesterone FPA test showed a drop in progesterone level on day 19. Cow #4 entered estrus on day 21.

FIG. 10 illustrates the reproductive cycle in Cow #5. The progesterone FPA test showed a drop in progesterone level on day 21. Cow #5 entered estrus on day 23.

DETAILED DESCRIPTION OF THE INVENTION

Figure 1:
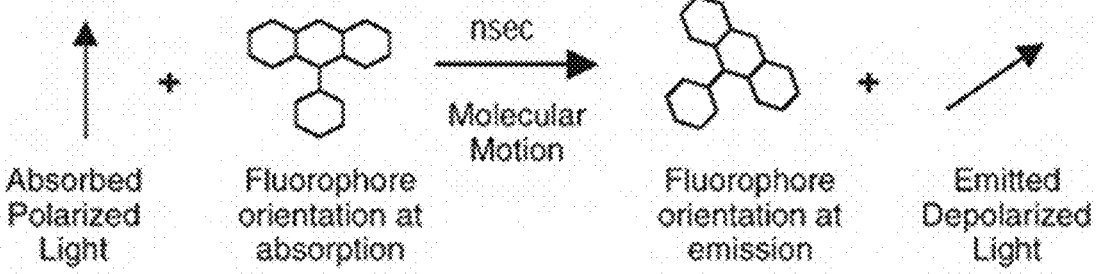
FIG. 1 shows depolarization of plane polarized light by a fluorophore that undergoes measure molecular rotation during its fluorescence lifetime, which is an underlying phenomenon in fluorescence polarization assay (FPA).

One aspect of the invention includes treating a sample to reduce riboflavin-dependent autofluorescence from the sample. "Riboflavin-dependent autofluorescence" refers to fluorescence emitted from a sample due to the presence of riboflavin. The treatment can include adding riboflavin binding protein to the sample, irradiating the sample, or a combination thereof.

The samples used in the invention can be any type of sample comprising an analyte. The sample may be a synthetic sample or a natural sample. The sample may be spiked with the analyte or naturally contain the analyte. The sample may comprise a bodily fluid or components purified therefrom. The bodily fluid may be from the body of an animal or a plant. Exemplary types of bodily fluids include intracellular fluids and extracellular fluids such as intravascular fluid (blood, plasma, serum), interstitial fluid, lymphatic fluid (sometimes included in interstitial fluid), transcellular fluid, and plant exudates. Exemplary bodily fluids include amniotic fluid, aqueous humour, vitreous humour, bile, blood, breast milk, cerebrospinal fluid, cerumen, chyle, chime, endolymph, perilymph, plasma, exudates, feces (such as diarrhea), female ejaculate, gastric acid, gastric juice, lymph, mucus (including nasal drainage and phlegm), pericardial fluid, peritoneal fluid, pleural fluid, pus, rheum, saliva, sebum (skin oil), serous fluid, serum, semen, smegma, sputum, synovial fluid, sweat, tears, urine, vaginal secretion, and vomit, among others.

Riboflavin binding protein (RBP) (also referred to in the art as RfBP or RFBP) is a phospho-glycoprotein, whose primary physiological function is to store riboflavin. RBP can be found in poultry plasma/serum, egg white, egg yolk, and in the plasma/serum of some mammalian species. An exemplary RBP suitable for use in the invention is the RBP from chicken egg white from Sigma-Aldrich, St. Louis, MO (Cat. No. R5258). Another exemplary RBP suitable for use in the invention is the RBP described by Hamazume et al. 1984. This RBP contains 219 amino acids with several post-translational modifications, including glycosylation and phosphorylation. Functional variants, orthologs and homologs of the exemplary RBPs are also suitable. The RBP-riboflavin complex lacks the characteristic fluorescence of free riboflavin, as up to 80% of the riboflavin fluorescence is quenched due to ligand binding between pH 6 and pH 9. The binding of riboflavin takes place at the hydrophobic cleft in the ligand binding domain where the vitamin's isoalloxazine ring is stacked between the parallel planes of Tyr 75 and Trp 156. This geometry and the proximity of other tryptophans explain the fluorescent quenching observed when riboflavin binds to the protein. RBP has binding capacity of 5-15 µg of riboflavin per mg of protein.

The RBP is preferably added in apo form (i.e., without bound riboflavin) in order to bind riboflavin present in the sample.

The RBP is preferably added to the sample in an amount by mass of about 0.1-100,000-fold of the amount by mass of riboflavin present in the sample, such as about 1-10,000-fold or 5-5,000-fold by mass of riboflavin present in the sample. Amounts above and below these preferred amounts are also acceptable.

For milk serum samples, the RBP is preferably added in an amount of about 10-100,000 µg/ml of sample, such as about 100-10,000 µg/ml of sample about 500-2,000 µg/ml of sample, or about 1,000 µg/ml of sample. Amounts above and below these preferred amounts are also acceptable.

The binding of RBP to riboflavin in the sample quenches the fluorescence of the riboflavin. Thus, while the RBP may be removed prior to fluorescence analysis of the sample, the RBP in preferred versions is not removed in order to omit a processing step.

To reduce riboflavin-dependent autofluorescence using irradiation, the sample is preferably exposed to visible light for a time sufficient to reduce the autofluorescence. The time may range from one minute or less to a day or more. Exemplary time ranges include about 1 minute to about 60 minutes or about 15 minutes to about 45 minutes. Light in the blue spectrum (455-485 nm) was found to be the most effective in reducing riboflavin-dependent autofluorescence. Thus, preferred versions of the invention irradiate the sample with light in this spectrum. The light used for irradiation preferably excludes UV light. The light used for irradiation may include or exclude light in the green spectrum (500-550 nm), yellow spectrum (570-590 nm), and/or the red spectrum (625 nm).

Clarification may be used to prepare the sample for fluorescence analysis, particularly samples comprising a milk product. As used herein, "milk product" refers to whole milk or any product derived or purified therefrom, including skim milk, reconstituted milk, evaporated milk, etc. "Milk serum" refers to a milk product from which casein, and preferably lipids, has/have been removed. Milk serum can be generated by coagulating casein in milk and removing the coagulated casein, preferably along with lipids, therefrom. The coagulating can comprise adding a rennet to the sample precursor in an amount sufficient to coagulate the casein. "Rennet" as used herein refers to any enzyme composition capable of coagulating casein. A large number of rennets are known in the art.

It is important not to destroy or remove the analyte in the clarification process. As some analytes may include antibodies or other proteins, it is important that the rennet used in the clarification and the conditions in which the rennet is used (e.g., time and temperature of rennet treatment) does not destroy these proteins. It was found that a microbial rennet from the fungus *Rhizomucor mihei* is capable of coagulating casein without destroying antibodies or other protein analytes. The *Rhizomucor mihei* rennet contains mucorpepsin and, unlike animal rennets, is devoid of other proteases such as pepsin and chymosin. Accordingly, rennet from *Rhizomucor mihei* may be suitably used in the present invention for detecting antibodies and other protein analytes. Other non-animal rennets, including microbial rennets, such as those from *Rhizomucor pusillus* and *Cryphonectria parasilica*, or vegetable rennets, such as cardoon rennet from *Cynara* (thistle), may additionally or alternatively be used. Animal rennets may additionally or alternatively be used.

The clarification process can comprise a rennet incubation step. The rennet incubation step preferably comprises incubating the sample in the presence of rennet at a first temperature for a first time period. When the analyte is a protein, the first temperature and first time period are selected to digest casein in the sample without destroying the protein analyte in the sample. An exemplary first temperature is a temperature from about 10° C. to about 37° C., such as from about 15° C. to about 30° C. or from about 20° C. to about 25° C. An exemplary first time period is a time period from about 10 seconds to about 60 minutes, such as from about 30 seconds to about 30 minutes, about 30 seconds to about 20 minutes, about 1 minute to about 10 minutes, or about 1 minute to about 5 minutes. Temperatures and time periods above and below these exemplary values are permitted.

In some versions, the clarification can optionally include a second incubation step after the rennet incubation step. The second incubation step can comprise incubating the sample at a second temperature for a second time period. The second temperature and second time period are selected to fully clarify the sample. The second temperature in the second incubation step is preferably a temperature lower than the first temperature in the first incubation step. An exemplary second temperature is a temperature from about 0° C. to about 10° C., such as about 2° C. to about 8° C. or about 4° C. An exemplary second time period is a time period from about 30 seconds to about 60 minutes, such as from about 2 minutes to about 30 minutes or about 15 minutes. Temperatures and time periods above and below these exemplary values are permitted.

In some versions, the rennet incubation step can be really short, such as less than a minute. In some versions, agents such as rennet, alcohol, and/or buffer are added to the samples at the first temperature, such as room temperature (20° C.). The samples can then be immediately placed in an environment at a second, lower temperature, such as a refrigerator set at, e.g., 4° C. The residual temperature of the sample in first 1 minute or so as it cools from the first temperature to the second temperature is enough to allow rennet to work. Precipitate forms as the sample cools.

The clarification preferably includes a separation step. If the clarification includes casein coagulation, the separation step is performed after the coagulation. If the clarification includes a second incubation step, the separation step is performed after the second incubation step. The separation step preferably comprises removing casein coagulant and/or other sample components, such as lipid, from the sample. The coagulant is preferably removed by centrifugation, filtration, or other methods. Filtration can be performed with a filter having a pore size from about 0.05 μm to about 20 μm, such as about 0.1 μm to about 10 μm. As used herein, "pore size" refers to a filter's ability to filter out particles with a diameter of the indicated size or larger. For example, a filter with a 0.2 μm pore size will filter out particles with a diameter of 0.2 μm or larger from a filtration stream. The filter can be a syringe filter, a vacuum filter, or any other type of filter and can be made of any material (ceramic, polymer, natural fiber, etc.).

It is important not to remove the analyte in the clarification process. It was found, for example, that hydrophobic analytes such as progesterone were removed along with the coagulated casein during the clarification process, thereby preventing their downstream detection. It was also found that adding a non-aqueous solvent to the sample during the clarification process can prevent analyte loss from the sample. Accordingly, preferred clarification processes for preparing samples for downstream detection of hydrophobic analytes include addition of a non-aqueous solvent prior to the separation step.

The non-aqueous solvent can be an organic solvent or an inorganic solvent. The non-aqueous solvent can be a non-polar solvent or a polar solvent. The polar solvent can be an aprotic polar solvent or a protic polar solvent. The protic polar solvent may be an alcohol.

Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether) 1,2-dimethoxy-ethane (glyme, DME) dimethylformamide (DMF) dimethyl sulfoxide (DMSO), 1,4-dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, and m-xylene.

Non-limiting examples of inorganic solvents include ammonia, liquid sulfur dioxide, sulfuryl chloride, sulfuryl chloride fluoride, phosphoryl chloride, dinitrogen tetroxide, antimony trichloride, bromine pentafluoride, hydrogen fluoride, pure sulfuric acid, and other inorganic acids.

Non-limiting examples of non-polar solvents include pentane, cyclopentane, hexane, cyclohexane, benzene, toluene, 1,4-dioxane, chloroform, diethyl ether, and dichloromethane (DCM).

Non-limiting examples of polar solvents include tetrahydrofuran (THF), ethyl acetate, acetone, dimethylformamide (DMF), acetonitrile, dimethyl sulfoxide (DMSO), nitromethane, propylene carbonate, ammonia, formic acid, n-butanol, t-butanol, isopropyl alcohol (IPA), n-propanol, ethanol, methanol, and acetic acid.

Non-limiting examples of aprotic polar solvents include tetrahydrofuran (THF), ethyl acetate, acetone, dimethylformamide (DMF), acetonitrile, dimethyl sulfoxide (DMSO), nitromethane, and propylene carbonate.

Non-limiting examples of protic polar solvents include ammonia, formic acid, n-butanol, t-butanol, isopropyl alcohol (IPA), n-propanol, ethanol, methanol, and acetic acid.

Non-limiting examples of alcohols include t-amyl alcohol, benzyl alcohol, 1,4-butanediol, 1,2,4-butanetriol, butanol, 2-butanol, n-butanol, t-butyl alcohol, denatured alcohol, diethylene glycol, ethanol, ethylene glycol, 2-ethylhexanol, furfuryl alcohol, glycerol, isobutanol, isopropyl alcohol, methanol, 2-(2-methoxyethoxy)ethanol, 2-methyl-1-butanol, 2-methyl-1-pentanol, 3-methyl-2-butanol, neopentyl alcohol, 2-pentanol, 1,3-propanediol, 1-propanol, and propylene glycol.

The non-aqueous solvent may be added to the sample at a final concentration of from about 1% v/v to about 70% v/v, such as from about 5% v/v to about 60% v/v, about 10% v/v to about 50% v/v, about 20% v/v to about 40% v/v, or about 33% v/v. Amounts above and below these values are acceptable.

"Hydrophobic" as used herein refers to compounds having an average solubility less than 1 mg/ml in distilled water at room temperature (20° C.), such as less than 100 μg/ml in distilled water at room temperature. The clarification processes of the invention can be used with samples containing analytes with an average solubility less than 1 mg/ml in distilled water at room temperature or less than 100 μg/ml in distilled water at room temperature. The clarification processes of the invention, for example, can be used with samples containing progesterone or other hydrophobic compounds as an analyte. Progesterone has an average solubility of 16.8 μg/ml in distilled water at room temperature.

The clarification methods of the invention can be used with any steroid hormones as an analyte. Suitable steroid hormones include corticosteroids, sex steroids. Suitable steroid hormones include natural steroid hormones and synthetic steroid hormones. Non-limiting examples of steroid hormones include testosterone, dehydroepiandrosterone, androstenedione, dihydrotestosterone, aldosterone, progesterone, estradiol, estrone, estriol, cortisol, calcitriol (1,25-dihydroxyvitamin D3), calcidiol (25-hydroxyvitamin D3), alclometasone, prednisone, dexamethasone, triamcinolone, cortisone, fludrocortisone, dihydrotachysterol, oxandrolone, oxabolone, testosterone, nandrolone, diethylstilbestrol (DES), estradiol, norethisterone, medroxyprogesterone acetate, hydroxyprogesterone caproate, cyproterone acetate, mifepristone, and gestrinone, among others.

The clarification methods can also be used with any other analyte or type of analyte described herein, among others.

In general, analytes of the invention include organic molecules, inorganic molecules, biological macromolecules (e.g., proteins, lipids, carbohydrates, nucleic acids), biological monomers (amino acids, fatty acids, monosaccharides, nucleotides), synthetic small molecules, and combinations thereof, among others. The analyte can be an antibody, an antigen, a hormone, a nutrient, a toxin, or any other type of molecule with any other type of function. As used herein, "antigen" refers to any molecule that binds specifically to an antibody. Particular subsets of antigens are molecules that induce an immune response (to produce an antibody) in a host organism. The analyte may be an antigen of a pathogen.

Samples suitably treated as described above can be used in any fluorescence-based assay. "Fluorescence-based assay" refers to any assay that involves the detection of fluorescence emitted from a sample. Examples include fluorescence microscopy, fluorescence lifetime imaging microscopy (FILM), fluorescent immunoassays (ELFIA), fluorescence microplate assays, fluorescence resonance energy transfer or Förster resonance energy transfer (FRET), fluorescent biosensing (fluorescent glucose biosensors), fluorescence anisotropy (FA), and fluorescence polarization assay (FPA), among others.

FPA and other fluorescence-based methods involve addition of a tracer to the sample. As used herein, "tracer" is used synonymously with "analyte tracer" and refers to any fluorescent compound capable of binding to an analyte or competing with the analyte for binding to a common ligand. The addition of a tracer can indicate the presence of an analyte in a sample either through directly binding to the analyte or competing with the analyte for binding to the ligand via a number of assay formats. Tracers that bind directly to the analytes are referred to herein as "direct tracers." Tracers that compete with the analyte for binding to a common ligand are referred to herein as "indirect tracers." "Ligand" is used herein to refer to any binding partner of a given compound. A ligand to which an analyte and an indirect tracer compete for binding is referred to herein as a "competition ligand."

The tracer may comprise a binding moiety and a fluorescent moiety. The binding moiety is a portion of the tracer that binds to the analyte or the ligand. The fluorescent moiety is a portion of the tracer that fluoresces. The fluorescent moiety can be chemically conjugated to the binding moiety or, in the case of protein tracers, can be expressed as a fusion protein with the binding moiety.

Binding moieties that directly bind to the analyte are referred to herein as "direct binding moieties." Exemplary direct binding moieties can include antibodies (for, e.g., antigen analytes), antigens (for, e.g., antibody analytes), and aptamers configured to bind to the analyte, among others. Binding moieties that compete with the analyte for binding to a competition ligand are referred to herein as "competing moieties." Exemplary competing moieties include standards of the analyte (e.g., synthesized or purified versions of the analyte) and aptamers configured to bind to the competition ligand, among others.

The fluorescent moiety can comprise any fluorophore. "Fluorophore" refers to any chemical compound that can re-emit light upon light excitation. Fluorophores can include fluorescent proteins or non-protein fluorophores. Fluorescent proteins include green fluorescent protein (GFP), yellow fluorescent protein (YFP), red fluorescent protein (RFP), blue fluorescent protein (BFP), etc. Examples of non-protein fluorophores include xanthene derivatives, such as fluorescein, rhodamine, Oregon green, eosin, and Texas red; cyanine derivatives, such as cyanine, indocarbocyanine, oxacarbocyanine, thiacarbocyanine, and merocyanine; squaraine derivatives and ring-substituted squaraines such as Seta, SeTau, and Square dyes; naphthalene derivatives, such as dansyl and prodan derivatives; coumarin derivatives; oxadiazole derivatives, such as pyridyloxazole, nitrobenzoxadiazole, and benzoxadiazole; anthracene derivatives, such as anthraquinones (DRAQS, DRAQ7 and CyTRAK Orange); pyrene derivatives, such as cascade blue; oxazine derivatives, such as Nile red, Nile blue, cresyl violet, and oxazine 170; acridine derivatives, such as proflavin, acridine orange, and acridine yellow; arylmethine derivatives, such as auramine, crystal violet, and malachite green; and tetrapyrrole derivatives, such as porphin, phthalocyanine, and bilirubin.

Some fluorescence-based assays comprise adding a tracer without a competition ligand. These assays typically employ direct tracers. Some fluorescence-based assays comprise adding a tracer and a competition ligand. These assays typically employ indirect tracers. Exemplary fluorescence-based assays using direct tracers or indirect tracers in combination with competition ligands are described below in the following examples.

After the tracer or the tracer and competition ligand is added to the sample, fluorescence emitted from the tracer is detected. Detecting fluorescence from the tracer in the sample can indicate the amount of the analyte in the sample using any of a number of assay formats. Depending on the assay format, the amplitude of the fluorescence, the wavelength of the fluorescence, and/or the polarization of the fluorescence detected can indicate the amount of analyte in the sample. In some assays, for example, unbound tracer may be washed or removed, and the amplitude of the detected fluorescence can indicate the amount of analyte in the sample. In assays such as FRET, the wavelength of the fluorescence can indicate the amount of analyte in the sample. In assays such as FPA the polarization of the fluorescence can indicate the amount of analyte in the sample. Various exemplary assays employing FPA are discussed in the following examples. "Amount of analyte" can refer to a quantitative or qualitative indication of the quantity of analyte present in a sample. In some versions, "amount of analyte" can indicate the mere presence or absence of analyte in a sample.

Some fluorophores are pH sensitive. Thus, prior to the detecting, some methods of the invention comprise buffering the sample to a suitable pH for emitting fluorescence from the fluorophore. For use of fluorescein as a fluorophore, for example, the sample is preferably buffered to have a pH of from about 6.5 to about 8.5.

In addition to the methods described herein, other aspects of the invention include any reagent or combination of reagents described herein, whether provided individually or in combination as a kit.

Kits of the invention, for example, may include a negative control, a positive control, a tracer, a sample diluent, RBP, a rennet, a clarification additive, or any combination thereof The negative control preferably includes a substance lacking the analyte. The positive control preferably includes a substance containing an analyte standard. The negative control and positive control are preferably composed of the same substance, save for the absence or presence of the analyte, respectively. The sample diluent may be a buffer suitable for buffering a sample to a suitable pH for the fluorophore to fluoresce. The clarification additive may comprise a rennet depending on the downstream application. Any of the negative control, the positive control, the tracer, the RBP, the rennet, may be provided in solid (lyophilized or dried powder, etc.) or liquid form (in a solvent, etc.). The kits may include instructions for use in accordance with the methods provided herein.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Example 1. Fluorescence Polarization

Principle of Fluorescence Polarization

Fluorescence polarization involves measuring the polarization of emitted light by excited fluorescing molecules. It is used to provide information concerning molecular size and energy. The bigger the molecule, the higher the polarization of the emitted light.

A schema showing fluorescence polarization is shown in FIG. 1. When a fluorescing molecule (a fluorophore) absorbs a polarized light beam, it emits depolarized light. During this period of light absorption, which is only a few nanoseconds ($10^{-9}$ sec), the molecule will enter an "excited state" after which it will emit a light of a different wavelength. This period is called "fluorescence lifetime," which is defined as the period between absorption of an excitation photon and the emission of a photon through fluorescence. Particles in solution have motion, which is known as Brownian motion. When a particle as small as a fluorophore (like fluorescein) rotates during the few nanoseconds of the fluorescence lifetime, this changes the plane of polarized light received. If the molecule binds to a receptor of a significantly greater size (like an antibody), the ability of the fluorophore to depolarize polarized light is severely reduced, since added molecular mass of the antibody (tracer+antibody) will greatly reduce molecular rotation over the fluorescence lifetime. This means less depolarization of the original plane polarized light.

Polarization assays are homogeneous; there is no necessity of separating free and bound ligand. There is no need of radioisotopes. Fluorescence polarization assays are reproducible and effortlessly automated. This, in addition to use of different kinds of fluorophores, including synthetic fluorophores, makes fluorescence polarization assays less costly than before.

Fluorescence polarization instruments typically measure emitted fluorescent light in two planes: parallel and perpendicular to the incoming excitation light. This permits measuring the amount of molecules able to turn 90 degrees during the fluorescence lifetime, as well as assessing the change in the size of the molecules. As discussed in further detail below, the amount of fluorescence in each plane is used in a formula to calculate polarization units (mP). Fluorescence intensity in each plane is measured in relative fluorescence units (RFU), which represent a photon count or light intensity. Because fluorescence polarization depends on a precise measurement of emitted light in a sample, it is important for the sample to be optically neutral and, thus, very clear of particulates and background. Particulates will depolarize light and will lead to erroneous measurements. The methods of the invention drastically improve the clarity of samples for fluorescence polarization assays.

Competitive Fluorescence Polarization Assay

One type of fluorescence polarization assay (FPA) is competitive fluorescence polarization assay (cFPA). In this assay platform, there are three main components:

1) Unknown amount of analyte;
2) Known amount of tracer (same compound as the analyte but labeled with fluorophore); and
3) Known amount of antibody (e.g., monoclonal antibody) against the tracer/analyte.

The principle of the competitive assay is that analyte molecules in the sample compete with the tracer for binding antibody. In the case of a low concentration of analyte, most or all of the tracer is bound to the monoclonal antibody, resulting in high polarization. In the case of a high concentration of analyte, the tracer remains unbound, resulting in low polarization. Polarization is inversely dependent on the concentration of the analyte. See, e.g., U.S. Pat. No. 6,812,036, which is incorporated herein by reference in its entirety, for an example of cFPA.

Fluorescence Polarization Assay Measurement and Results

Figure 2:
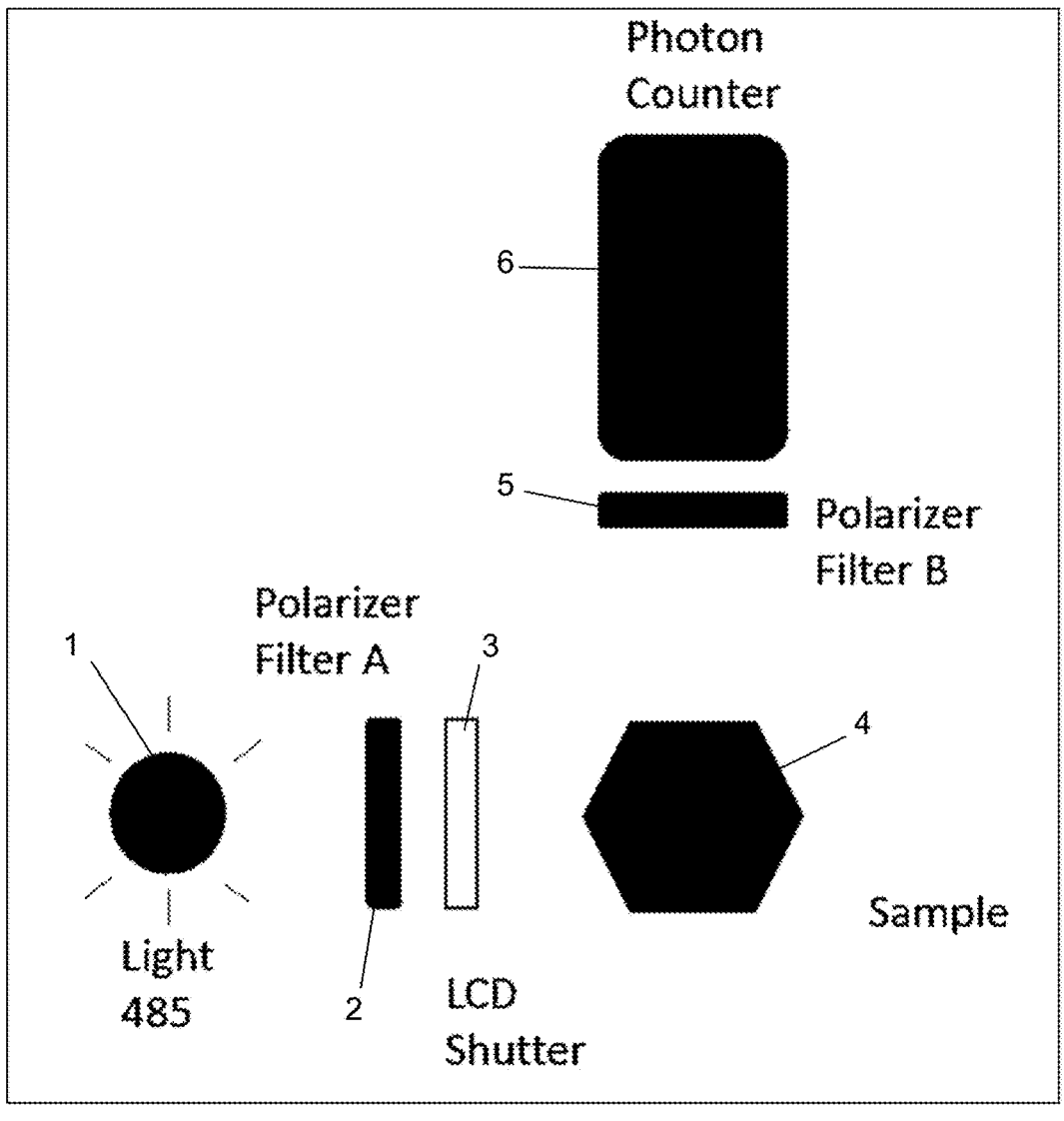
FIG. 2 shows a schematic of an exemplary FPA device.
Figure 6:
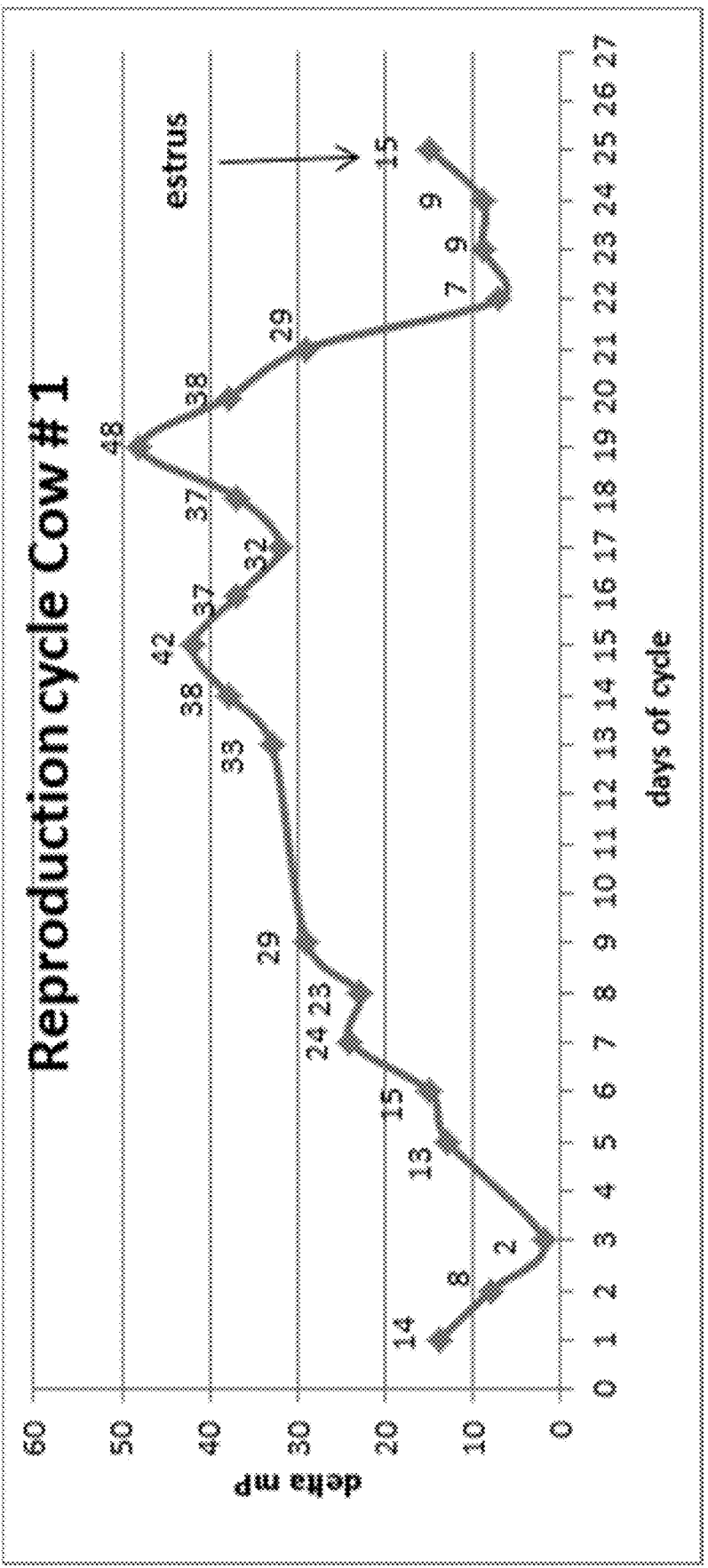
FIGS. 6-10 illustrate a reproductive (estrus) cycle in each of 5 cows (Cows #1 through #5). In each of FIGS. 6-10, the X axis displays the days of the reproductive cycle, and the Y axis displays progesterone levels during the reproductive cycle in delta mP values as detected by FPA.
Figure 7:
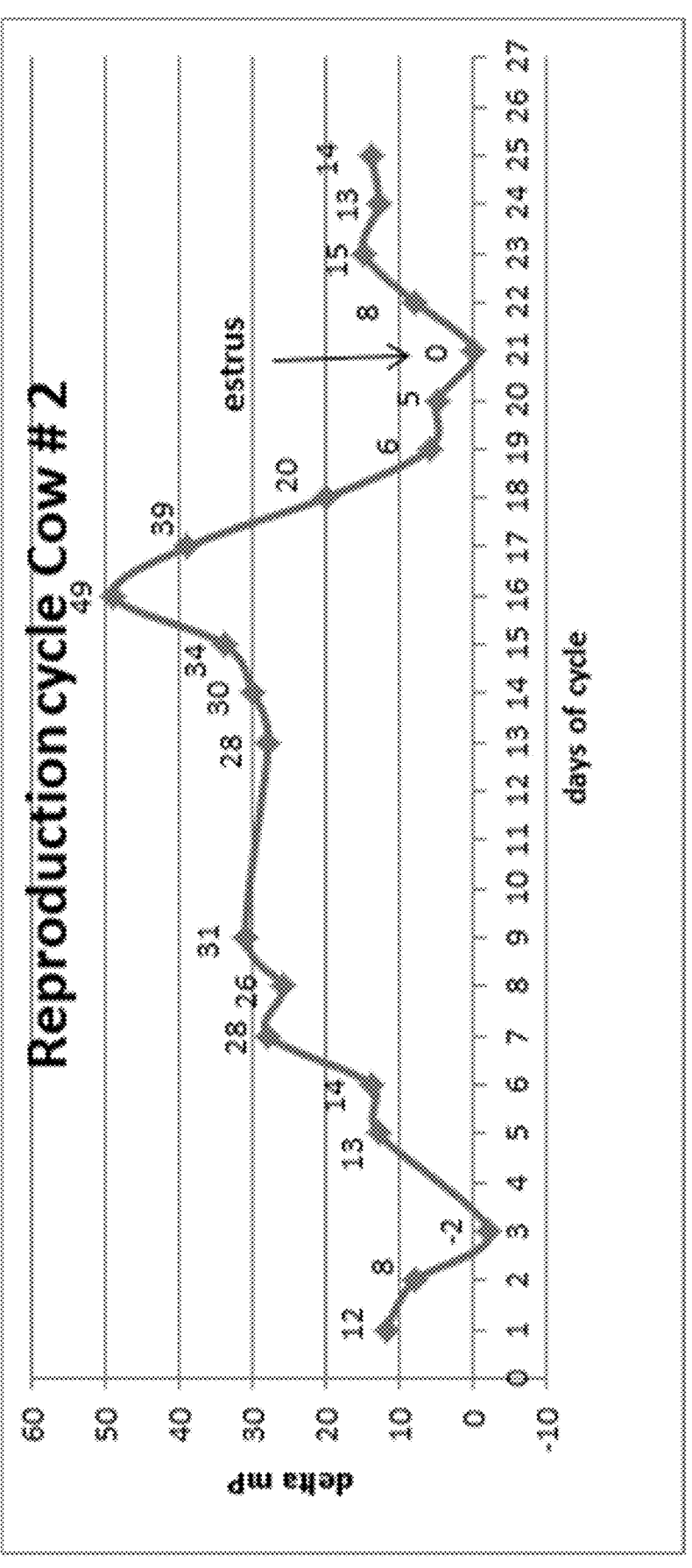
Figure 8:
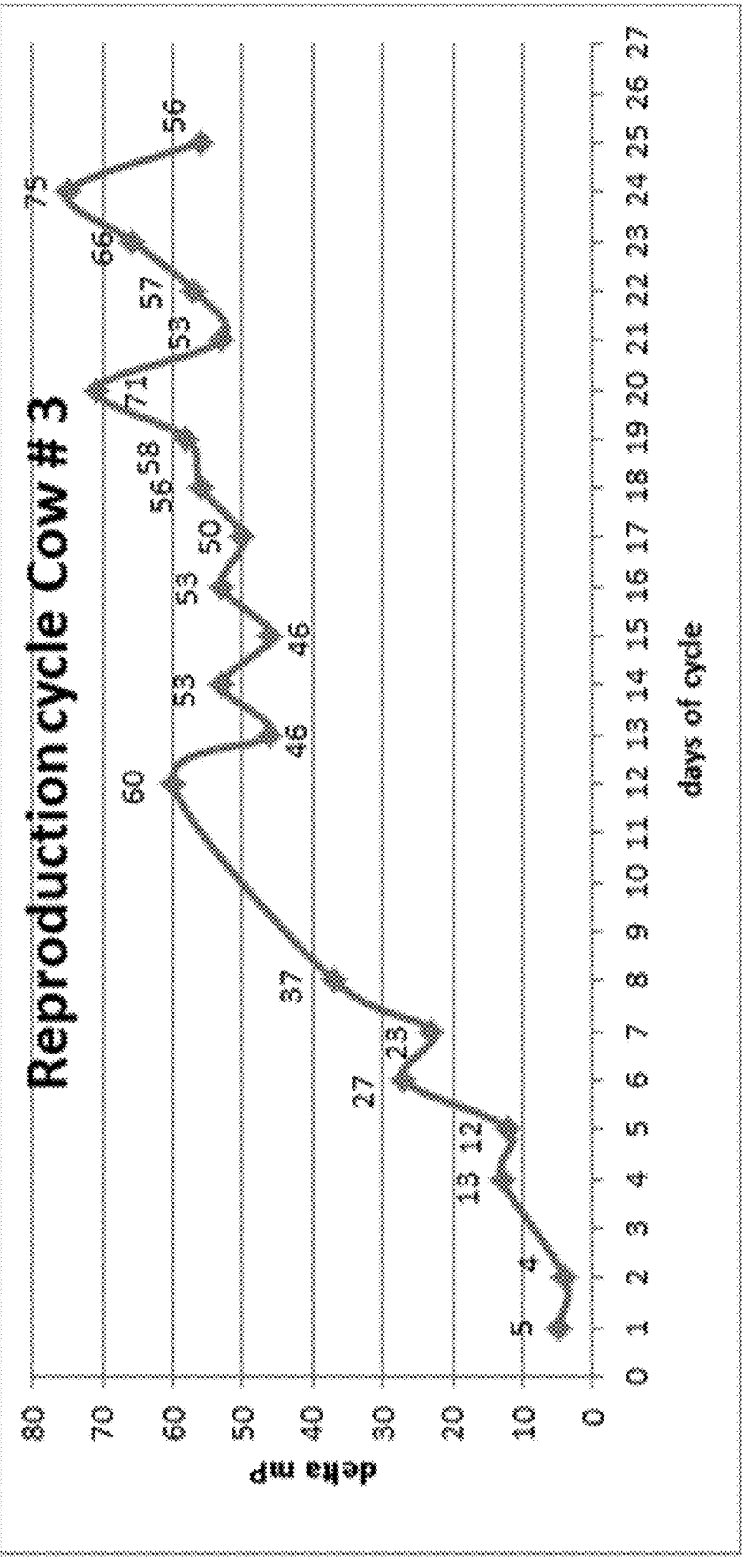
Figure 9:
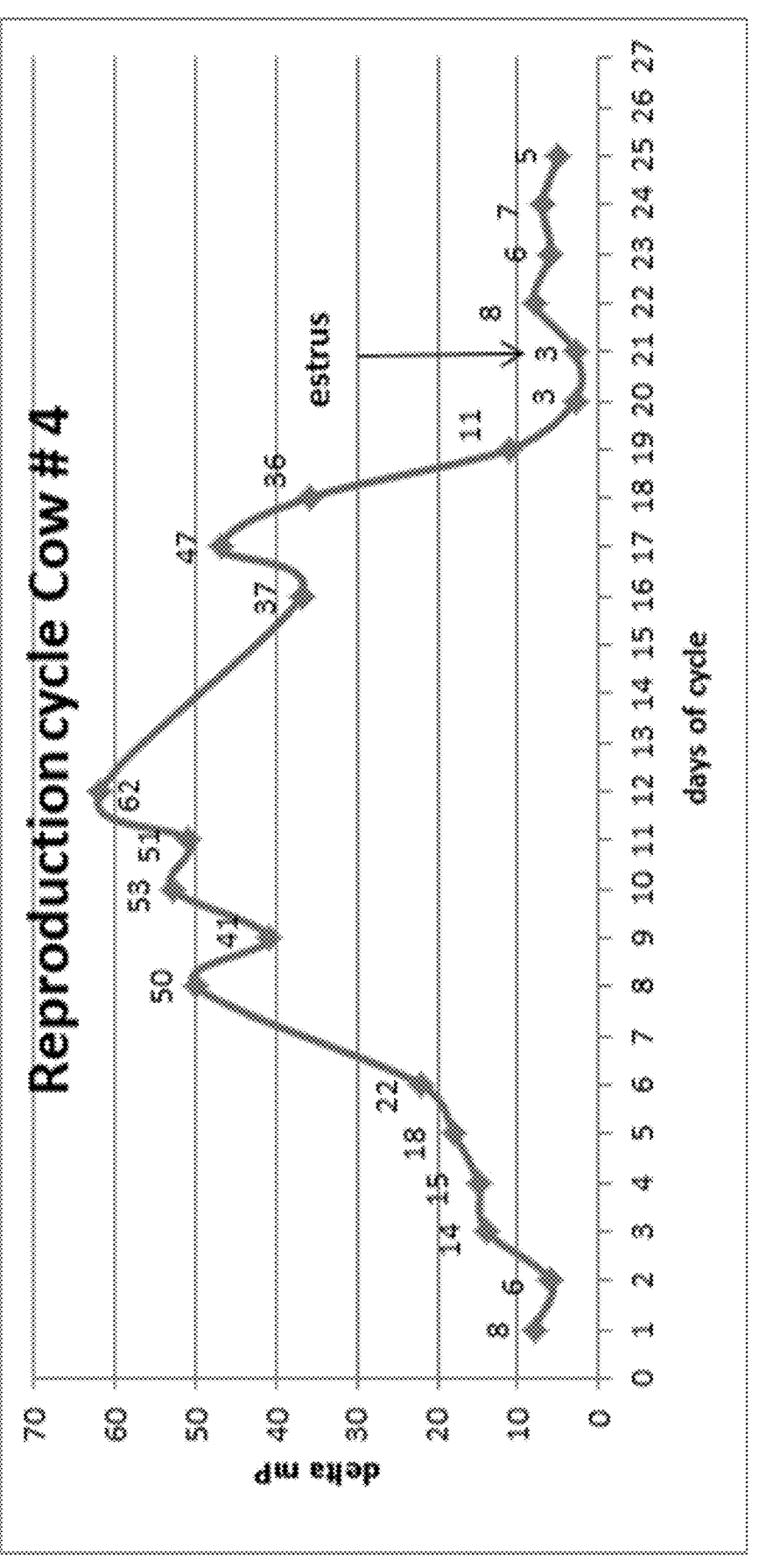
Figure 10:
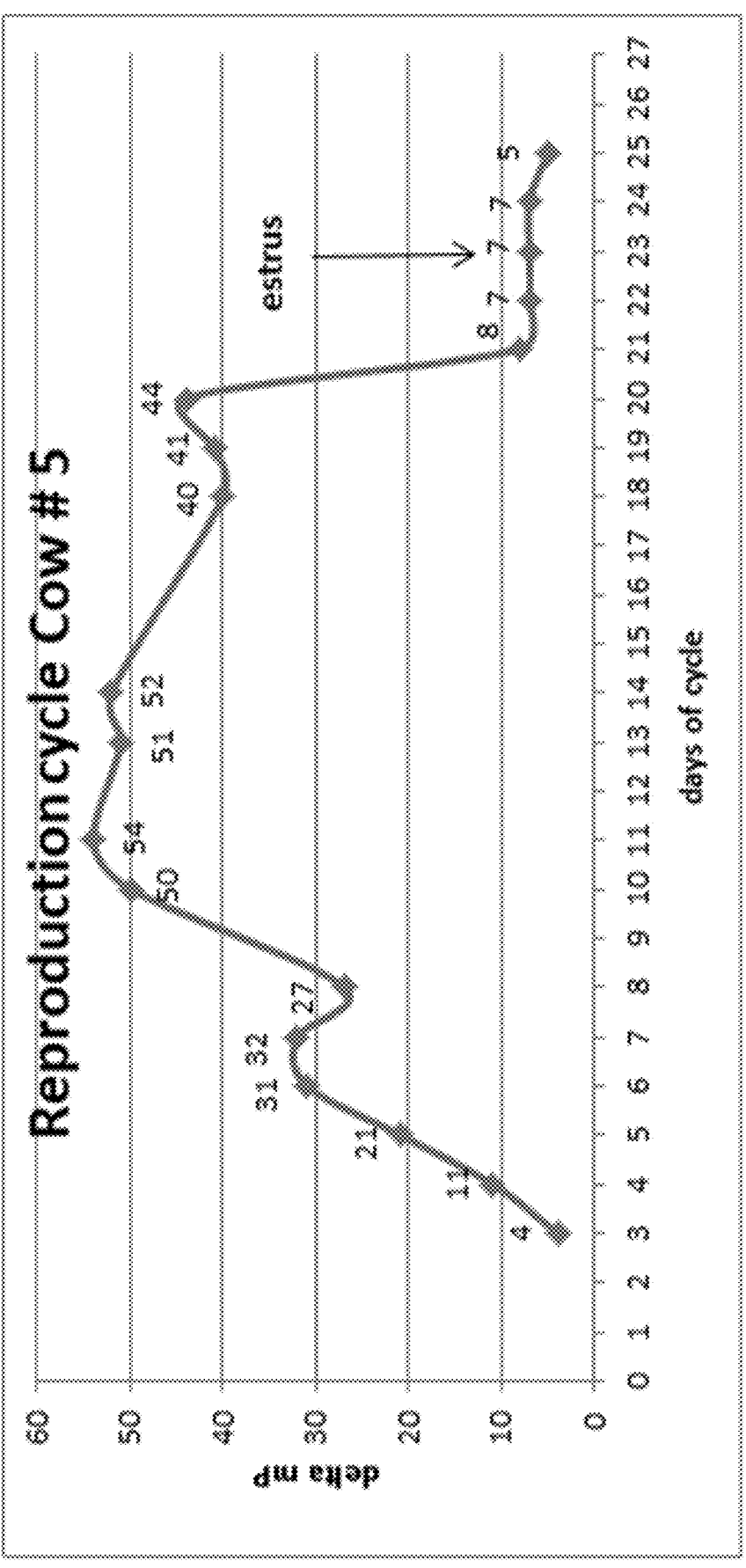

In fluorescence polarization two measurements are taken. Referring to FIG. 2, a light 1 (e.g., 485 nm) is polarized with a first polarizing filter 2 (Polarizer Filter A). It then hits the sample 4 and causes fluorescence of tracer molecules oriented parallel to the incoming light. These then emit photons of, e.g., —525 nm. The photons go through a second polarizing filter 5 (Polarizer Filter B), which is oriented parallel to the first filter 2 and hits the photon counter 6, which counts the photons. This reading is referred to as a "parallel" or "vertical" (V) reading.

An LCD shutter 2 then switches the polarization of the light 1 by 90 degrees and causes fluorescence of tracer molecules in the sample 4 perpendicular to the polarizing filters 2,5 (Polarizers A and B). These molecules will turn due to Brownian movement, and 535-nm photons parallel to the second polarizing filter (Polarizer B) will pass to the photon counter 6. This reading is referred to as a "perpendicular" or "horizontal" (H) reading. If tracer molecules that are fluorescing have a lot of energy and turn fast, many of them will turn by 90 degrees, which will result in similar readings between the vertical (V) and horizontal (H) positions.

A formula is applied to calculate that ratio of photons counted in both planes. Units of the ratio are arbitrary and called milli-P or mP. The formula is:

$$mP = (V-H)/(V+H)*1000$$

A correction factor is applied to the horizontal reading, which is there to normalize readings between different instruments. This is called the "G-factor." The formula with the correction factors is as follows:

$$Mp = (V-H*G)/(V+H*G)*1000$$

Before taking the V and H fluorophore readings outlined above, a V and H blank reading of the sample is taken, which is then subtracted from the V and H fluorophore readings, respectively. In a typical procedure, the blank reading is taken before the fluorescent tracer is added to the mix. An example of a result from these measurements using methods of the invention is shown in Table 1.

TABLE 1

| | | Example of FPA readings. | | | |
| --- | --- | --- | --- | --- | --- |
| | V Blank | H Blank | V Fluor | H Fluor | mP |
| Negative | 33971 | 14839 | 195894 | 155913 | 82.9 |
| Positive | 62547 | 27249 | 216175 | 142488 | 156.7 |

If the blank readings are 50-100 times higher than those shown in Table 1, for example around 1,000,000, then any reading of the fluorophore will be masked by the huge background. This will produce unreliable mP results. At least one aspect of the invention eliminates the influence of sample background by reducing riboflavin fluorescence.

Example 2: Detection of Progesterone Levels in Milk Samples Using Fluorescence Polarization Technology Summary Progesterone is one of the most important hormones regulating reproductive cycles in mammals. Progesterone levels can be an indicator of estrus and consequently pregnancy, as well as some pathological conditions. There have been multiple previous attempts to create an assay or method for detecting progesterone levels in milk samples of cattle to aid in the reproductive performance of herds. These previous attempts are only partially effective, as all of the assays are difficult to perform and inaccurate. One of the main reasons for the inaccuracy is the hydrophobic nature of the progesterone molecule, which requires solvents to extract and keep the progesterone in solution. For the same reason, the molecule resists binding to solid phases that are employed in many of the previous assays, such as enzyme-linked immunosorbent assays (ELISAs) and lateral flow assays.

The present example describes a fluorescence polarization method for detection of progesterone in milk samples of cows. The assay is homogeneous, does not require a solid phase, and can be done successfully in the presence of solvents. Earlier attempts (Hong et al. 2002) to develop assays based on fluorescence polarization in milk have resulted in insufficient sensitivity of methods for three reasons. The first reason is the variable pH of milk samples, which causes quenching of fluorophores used in the assay. The second and more important reason is the high natural fluorescence of milk samples (background) due to the high concentration of riboflavin. The third reason is the scattering of light by the casein molecules and non-transparent nature of milk samples.

The exemplary method described herein solves all of the above-mentioned obstacles and produces accurate results in measuring concentrations of progesterone. The method extracts and keeps progesterone in solution using a non-aqueous polar solvent (e.g., alcohol), clarifies milk samples using milk whey produced by milk-coagulating enzymes and separation by, e.g., centrifugation and/or filtration, quenches background fluorescence using riboflavin binding protein or by exposing samples to intensive light source, and stabilizes the pH of milk using strong buffers. Lowering background fluorescence allows for use of a high-concentration sample, which results in very high sensitivity. The resulting sensitivity is sufficient for reliably detecting physiological concentrations of progesterone.

Background

Today's dairy farms are under increasing pressure to maintain high productivity. The amount of milk produced by cows has increased from 20,204 liters per cow in year 2007 to 22,775 liters per cow in 2016 in the United States of America (USDA data). At the same time, the proportion of cows that become pregnant after first insemination post calving has decreased from 50% in the 1950s to only 33% today. The reason for this decrease is high milk production, which stresses the animal's metabolism and consequently decreases its reproductive capabilities. Many animals do not show signs of estrus (silent estrus), which makes it difficult to determine the best time for insemination. More than ever, technology is needed to help farmers make these decisions.

The ideal technology would be a simple test which can be run in the field (cow side) and can produce accurate and repeatable results.

Progesterone as a Cycle Regulator

The steroid hormone progesterone (P4) plays a key role in the reproductive events associated with establishing and maintaining pregnancy in animals. Its main role is in regulating the estrous cycle.

The average estrous cycle length in dairy cows is approximately 21 days but can vary between 17 and 24 days and still be considered normal. The length of the estrous cycle is measured as the time between two consecutive estrus or heat periods. The physiological and hormonal changes which occur in the female over the estrous cycle prepare the reproductive tract for estrus (the period of sexual receptivity), ovulation (release of the egg) and implantation (attachment of the fertilized egg to the uterus).

On the first day of the cycle, the cow is in estrus and is preparing for fertilization. The progesterone level in the cow at this time is low, and the estrogen level is high. Under the influence of estrogen, the cervix dilates slightly, and cervical mucus becomes less sticky to allow easier penetration of spermatozoides.

During the next five days, the corpus luteum grows rapidly in both size and progesterone-secreting capability. Granulosa and thecal cells, now referred to as the corpus luteum, continue to divide rapidly and change from estrogen- to progesterone-secreting cells. Progesterone stimulates the uterus to produce uterine milk, which nourishes the fertilized egg or embryo.

From days 6 to 16 the corpus luteum continues to develop and reaches its maximum growth and function by days 10 to 12. The circulating level of progesterone, produced by the mature corpus luteum, is high and inhibits development of an ovulatory gonadotropin surge.

From days 16 to 19, if the animal does not conceive, the corpus luteum begins its regression or death due to secretion of prostaglandin F2a by the uterus. The progesterone level rapidly decreases in the blood stream.

On days 19-20, the estrogen level rises, produced by the rapidly growing follicles, which stimulates reproductive tract preparation for standing estrus.

Chemical Structure and Characteristics of the Progesterone Molecule

Progesterone is a steroid hormone. A steroid is a group of natural or synthetic, fat-soluble, organic compounds belonging to the class of lipids and characterized by a molecular core of four fused rings totaling 17 carbon atoms: three six-carbon rings and one five-carbon ring fused together. The type of steroid is determined by the three-dimensional configuration and the type of additional side chains and rings. Progesterone is a type of progestogen, a subset of sex steroids, with androgens and estrogens being the other major sex steroids.

Progesterone contains ketone and oxygenated functional groups, as well as two methyl branches. Like all steroid hormones, progesterone is hydrophobic. This is mostly due to the absence of polar functional groups.

Progesterone, like all other steroid hormones, is synthesized from pregnenolone, a derivative of cholesterol. This conversion takes place in two steps. The 3-hydroxyl group is converted to a keto group and the double bond is moved to C-4 from C-5. See FIG. 3.

Advantages of Detecting Progesterone in Milk Using Fluorescence Polarization Technology Efficient livestock production requires accurate, early pregnancy detection. Pregnancy diagnosis is an important part of the reproductive program on most dairies. Finding open cows is the most important aspect of pregnancy diagnosis. Cows that are pregnant do not need further reproductive attention.

The primary advantage to early pregnancy diagnosis is the ability to find open cows quicker and get those cows enrolled back into the current farm production system. The poorer the heat detection is on the farm the more important it is to consider early pregnancy diagnosis. The time interval between herd health visits also affects the advantages of early pregnancy diagnosis. The early identification of non-pregnant cattle is important, as treating these non-pregnant cattle differently provides the economic benefit of pregnancy tests.

The simple and rapid progesterone test described herein can be used to detect a low progesterone level in milk and thereby identify cows that fail to become pregnant after artificial insemination. This can reduce the open period in cows and avoid losing one or more estrus cycles.

Milk as a Sample for Fluorescence Polarization Technology

From a dairy cow-handling aspect, the use of a milk-based pregnancy test as described herein reduces the amount of stress inflicted on the animals. The milk samples can be taken in the parlor without the need of special training the employees. In contrast to blood-based pregnancy tests, taking these samples does not require the use of needles to collect samples.

Because the samples can be taken in the parlor, there is no need for dairy cows to be locked up, thereby eliminating any additional disruptions in the dairy cow's resting and eating times. The milk-based test described herein provides a non-invasive way of confirming a pregnancy, while eliminating additional labor requirements of other pregnancy diagnosis methods.

Additionally, dairy producers can develop protocols that work for their individual operations, taking into consideration the time frame and frequency at which milk samples should be taken for pregnancy detection.

However, milk as a sample has previously caused problems in fluorescence-based assays due to its autofluorescence. Autofluorescence reduces the signal-to-noise ratio, which creates problems in distinguishing weak signals of low concentration analytes like progesterone from the background fluorescence. Riboflavin, also known as vitamin B2 is the main cause of milk serum autofluorescence. Concentrations of riboflavin in milk range from 0.6 to 3.42 mg per liter. In aqueous solutions like milk, all forms are unstable when exposed to visible and ultraviolet light.

Challenges in Detecting Progesterone

The progesterone molecule is a hydrophobic molecule (highly insoluble in water) and, consequently, is very hard to detect in a simple laboratory setting.

ELISA tests are dependent on immobilizing an analyte on a solid phase and washing off unbound substrate. For immobilization, highly specific, monoclonal antibodies are used. In the case of hydrophobic molecules like progesterone, the process of immobilization can fail either at the phase of indirect binding of the molecule to the solid phase or washing off the molecule during the removal of undesired substrate. At the level of less trained technicians, this process usually results in inaccurate detection of the level of progesterone. Historically this has caused a loss of confidence in progesterone assays. Previous papers published show lack of consistency and low sensitivity of FPA assays for detecting progesterone. See Varriale et al. 2015 and Hong et al. 2002.

Treatment of Milk for Clarity and Progesterone Extraction

Before subjecting to FPA, a milk sample is treated to generate milk serum (whey). A buffer containing rennet enzymes from *Rhizomucor mihei* can be used as an animal rennet substitute for this process. The *Rhizomucor mihei* enzymes are very stable at various temperatures and do not degrade antibodies or other protein analytes in milk at the exemplary temperatures and time periods provided herein. Treatment with the *Rhizomucor mihei* enzymes coagulate casein in milk, and the coagulated casein can be subsequently removed to result in milk serum. The milk serum is transparent and suitable for testing with fluorescence-based assays.

An exemplary buffer containing the *Rhizomucor mihei* rennet enzymes is referred to in the present examples as "ClearMilk Buffer." ClearMilk Buffer is phosphate buffered saline (PBS) pH 5.8 with *Rhizomucor mihei* rennet enzymes present in an amount of 750 IMCU/ml (International Milk Clotting Units/milliliter).

For analytes, such as progesterone or other hydrophobic analytes, the presence of a non-aqueous solvent in the clarification process is important for maintaining the analyte in the milk serum and preventing its separation therefrom with the coagulated casein or lipids. The non-aqueous solvent may comprise a non-aqueous polar solvent. The non-aqueous polar solvent may comprise an alcohol. The alcohol may comprise ethanol.

To generate milk serum for the detection of progesterone, ethanol was added to milk to a final concentration of about 33% v/v. ClearMilk Buffer was added to the milk/alcohol mixture in a volume ratio of about 1:16 (ClearMilk Buffer: milk/alcohol mixture). The resulting mixture (FIG. 4) was then incubated for indicated lengths of time at indicated temperatures, and a firm clot of casein formed. The mixture was then centrifuged at approximately 10,000×g for 5 minutes in a microcentrifuge. This process separated the mixture into three layers (FIG. 5): (1) A casein clot on the bottom; (2) Clear milk serum in the middle; and (3) A thin layer of lipids on the top. Alternatively, the mixture was filtered through a filter syringe to generate milk serum. The resulting milk serum was then used for detecting progesterone. As described in further detail below, the presence of alcohol was important for maintaining progesterone in the milk serum, rather than, e.g., in the casein layer or the lipid layer.

Variability of pH of Milk Samples and Effect on Test Results

Fresh milk from the cow typically has a pH between 6.5 and 6.7 (slightly acidic). The pH of milk changes over time.

As milk goes sour, it becomes more acidic and the pH lowers. This occurs as bacteria in milk convert the lactose sugar into lactic acid. In cases in which the cow has mastitis, the pH of the milk is higher (more basic). These differences in pH are very important for FPA because of the pH's influence on fluorophore (tracer) fluorescence. Acidic or alkaline pHs decrease (quench) the fluorescence intensity of the fluorophore, rendering large portion of active molecules undetectable. The ideal pH for fluorescein is around 7.5. Strong buffers can be used to compensate for the pH variability in different milk samples, which is important to avoid variability of results. An exemplary buffer is 1M Tris pH 7.7 with 0.1% (v/v) EDTA, which can be used at buffer:milk serum volume ratio of about 2.3:1.

Progesterone Tracer Preparation

An exemplary FPA assay described herein for detecting progesterone is a competitive FPA (cFPA) assay. A fluorescein-labeled progesterone tracer for this assay was made using the procedure described by Hong et al. 2002. The carboxyl group of progesterone-3-(O-carboxymethyl-oxime) (P-3CMO) was coupled with the amine group of fluorescein amidite label (FAM) to give a stable amide group. The progesterone tracer was purified using thin layer chromatography (TLC) using $CHCl_3$:$CH_3OH$ as a solvent in 4:1 (solvent:tracer) volume ratio. The functionality of the progesterone tracer was tested using a monoclonal antibody. The concentration of the progesterone tracer was set to match fluorescence intensity of 1 nM of fluorescein in 0.01 M phosphate buffer pH 7.2. Ten microliters of progesterone tracer in 1 ml of sample diluent had an intensity of around 100,000 relative fluorescence units (RFU) on a reference SENTRY® (Ellie LLC, Waukesha, WI) 200 instrument. As the fluorescence is described in relative fluorescence units, same instrument was used to check the fluorescence intensity of tracer and milk serum samples to determine the concentration. Ready-to-use progesterone tracer was prepared in 80% (v/v) DMSO plus 20% (v/v) 0.01 M PBS pH 7.3.

Monoclonal Antibody

A monoclonal antibody against progesterone (Cat. No. MBS633645) was purchased from Mybiosource, Inc. (San Diego, CA, USA). The immunogen for this antibody was progesterone-11a-hemisuccinate in a mouse. This antibody can be used for recognition of all species of progesterone. It demonstrates minimal cross-reactivity with following steroids: 17a-hydroxyprogesterone (0.8%); 3b-hydroxypregn-5-en-20-one (<0.1%); 20a-dihydroprogesterone (0.1%); testosterone (<0.1%); 17b-estradiol (<0.1%); and cortisol (<0.1%). The isotype of the antibody is IgG1,k. The clone number of the antibody is 0.N.521.

Reducing Background by Photodegradation of Riboflavin

The emission characteristics of the light radiation source play a significant role in the photodegradation of riboflavin. Around 30% of riboflavin is destroyed by sunlight in milk within only 30 minutes of exposure. In the dark, riboflavin is stable and remains unchanged under specified conditions for prolonged periods of time. In the dry form, riboflavin is only slightly affected by light, while in solution form it is rapidly degraded to various photoproducts through a variety of reactions under aerobic and anaerobic conditions. UV and visible light spectra are responsible for photodegradation of riboflavin, but when riboflavin is exposed to UV light, large quantities of photoproducts are produced, and the background does not drop. Only the visible light spectrum degrades riboflavin and also the high fluorescence background. The reactions involved in photodegradation of riboflavin include photoreduction, photoaddition and photo dealkylation. In developing methods of photodegradation, different light sources were used. These ranged from LED diodes to xenon lamps. The results were the same independent of source (e.g., riboflavin degradation with low background fluorescence), with the only difference being the time needed for completing the process.

An exemplary method of photodegradation was performed as follows. Different amounts of milk serum were diluted with buffer in 1.5-ml microcentrifuge tubes and placed in a chamber for light treatment. During this process, the antibodies and other molecules like progesterone remained stable in the solution, while milk serum lactalbumins and lactoglobulins precipitated. After light treatment, the sample was centrifuged in a microcentrifuge. The resulting supernatant can be used for any type of fluorescence polarization assay. A complete procedure is described below:

1. Prepare ready-to-use progesterone tracer in 80% DMSO, 20% 0.01 M PBS pH 7.3 with fluorescence intensity around 108,000 RFU on a SENTRY® (Ellie LLC, Waukesha, WI) 200 instrument;
2. Prepare ready-to-use anti-progesterone antibodies in a dilution of 1:130 (volume:volume) in 0.01 M PBS pH 7.3;
3. Prepare control diluent by mixing one part of solvent used in extraction (99.9% alcohol) and 9 parts of sample diluent (1 M Tris buffer pH 7.7 with 0.1% EDTA);
4. Mix small part of samples being tested for use as negative control;
5. Transfer 1.5 ml of milk as negative control into three microcentrifuge tubes;
6. Transfer 1 ml of milk samples into microcentrifuge tubes;
7. Add 500 µl of solvent (99.9% alcohol) in the microcentrifuge tubes with the samples;
8. Add 60 µl of ClearMilk Buffer in all tubes containing controls and samples;
9. Mix well;
10. Incubate for 10 minutes at room temperature;
11. Incubate for 15 minutes at +4° C.;
12. Centrifuge controls and samples at 10,000×g for 5 minutes;
13. Mix 400 µl of samples and controls and 1000 µl of 1M Tris buffer pH 7.7 with 0.1% EDTA in the new microcentrifuge tube;
14. Incubate samples and control in a light treatment chamber for 30 minutes;
15. Centrifuge samples and controls in a microcentrifuge at 10,000×g for 5 minutes;
16. Transfer 1 ml of supernatant into borosilicate glass tubes;
17. Add 10 µl of antibodies in all tubes containing controls and samples;
18. Mix well;
19. Incubate for 5 minutes at room temperature;
20. Read blank;
21. Add 10 µl of progesterone tracer in all tubes containing controls and samples;
22. Mix well;
23. Incubate for 15 minutes;
24. Read progesterone tracer and obtain mP values;
25. Calculate delta mP values.

The influence of different wavelengths of light on sample autofluorescence is shown in Table 2. The background fluorescence of samples treated with different wavelengths of light was measured with a fluorometer in relative fluorescence units (RFU). As shown, visible light in the blue spectrum was most efficient in reducing sample background fluorescence. Therefore, in further experiments, we used an intensive light source based on an LED with a bright light spectrum, which has a peak wavelength in the blue spectrum.

TABLE 2

| Influence of different light wavelengths on sample background autofluorescence. | |
| --- | --- |
| Sample | Sample Background in RFU |
| Non treated sample | 421616 |
| Whole light spectrum treated sample | 41803 |
| Blue spectrum (455-485 nm) | 38702 |
| Green spectrum (500-550 nm) | 46254 |
| Yellow spectrum (570-590 nm) | 56580 |
| Red spectrum (625 nm) | 54336 |

Reducing Background Fluorescence Using Riboflavin Binding Protein (RBP)

To test the effect of RBP in quenching autofluorescence in milk serum, different amounts of milk serum were diluted in buffer and RBP was added. The concentration of RBP sufficient to quench autofluorescence depended on the amount of milk serum used in the test. Eight hundred and fifty micrograms was the minimal amount of RBP needed to completely remove riboflavin fluorescence in 1 ml of milk serum. The reaction between RBP and riboflavin was almost instantaneous, and the sample was capable of being used for any type of FPA assay.

A comparison between photodegradation and RBP treatment in reducing autofluorescence in a milk serum-containing sample is shown in Table 3.

TABLE 3

| A comparison between photodegradation and RBP treatment in reducing riboflavin autofluorescence in a milk serum-containing sample. | |
| --- | --- |
| Sample | Sample Background |
| Non treated sample | 718308 |
| RBP treated sample | 64069 |
| Light treated sample | 65142 |

The efficacies of RBP treatment and photodegradation were comparable for reducing autofluorescence. In this regard, RBP treatment is a preferred method due to its simplicity and time savings. However, any embodiment employing RBP treatment described herein can use photodegradation in place of the RBP treatment.

Preliminary Test with Progesterone-Spiked Samples

The detection of progesterone using cFPA in milk serum was tested with progesterone-free samples spiked with different concentrations of progesterone standard (Sigma-Aldrich P0130-25G). Milk serum was prepared from a milk sample from a cow in visible estrus without alcohol solvent. This milk serum was then tested by radioimmunoassay (RIA) for progesterone, which shows non-detectable levels of progesterone in the sample (0.19 ng/ml). The milk serum was then spiked with 2, 4, 6, 8 and 10 ng/ml of progesterone. A complete procedure of the test is described below.

1. Prepare ready-to-use progesterone tracer in 80% DMSO, 20% 0.01 M PBS pH 7.3 with fluorescence intensity around 108,000 RFU on a SENTRY® (Ellie LLC, Waukesha, WI) 200 instrument;

2. Prepare ready-to-use anti-progesterone antibodies in a dilution of 1:130 (volume:volume) in 0.01 M PBS pH 7.3 containing riboflavin binding protein at a concentration of 28.5 mg/ml;
3. Transfer 1 ml of milk sample into 6 microcentrifuge tubes;
4. Add 60 µl of ClearMilk Buffer in all tubes containing samples;
5. Mix well;
6. Incubate for 15 minutes at +4° C.;
7. Centrifuge samples at 10,000×g for 5 minutes;
8. Milk will separate into three layers:
   Lipid layer on the top;
   Milk serum in the middle;
   Casein at the bottom;
9. Transfer 300 ul of milk serum from the middle layer from each tube into borosilicate glass tubes;
10. Add 700 ul of Sample Diluent;
11. Spike the borosilicate glass tubes with 10 ul of 2 ng/10 µl, 4 ng/10 µl, 6 ng/10 µl, 8 ng/10 µl, or 10 ng/10 µl solution of progesterone (progesterone dissolved in DMSO)
12. Mix well;
13. Add 10 µl of antibodies in all tubes containing samples;
14. Mix well;
15. Incubate for 5 minutes at room temperature;
16. Read blank;
17. Add 10 µl of progesterone tracer in all tubes containing samples;
18. Mix well;
19. Incubate for 5 minutes;
20. Read progesterone tracer and obtain mP values;
21. Calculate delta mP values.

The progesterone FPA assay showed very high sensitivity in detecting very low concentrations of progesterone, e.g., down to 1 ng/ml. It also showed large differences in polarization between very low concentrations of the analyte as shown in Table 4.

TABLE 4

| High sensitivity of the competitive progesterone FPA assay in detecting low progesterone concentrations in milk. | |
| --- | --- |
| Amount of Progesterone ng/ml | FPA results in mP values |
| 0 | 273 |
| 2 | 200 |
| 4 | 173 |
| 6 | 160 |
| 8 | 148 |
| 10 | 142 |

Progesterone FPA Test Results

The detection of progesterone using cFPA in milk serum from in-field milk samples was tested. Five Simmental breed cows of different ages and reproductive history were selected for this experiment. The experiment lasted 33 days in total. All cows were observed and examined for signs of estrus, presence of the follicle in estrus, and presence of the corpus luteum during luteal phase of the cycle. Cows 1, 2, 3, were introduced in estrus using PGF2α, while Cows 4 and 5 entered naturally into a cycle. Only Cow 3 was artificially inseminated. All other cows were let go through the cycle without insemination.

The characteristics of the cows were as follows. Cow 1 was four years old with prolonged estrus cycle and visible estrus without reproductive disorders. Cow 2 was two-anda-half years old with silent estrus. Cow 3 was twelve years old with low conception rate because of a previous uterine right horn injury during the calving. Cow 3 was inseminated during this experiment. Cow 4 was six years old with a normal cycle and estrus signs. Cow 5 was 16 years old with prolonged estrus cycle and normal estrus signs. Progesterone levels were measured using the competitive Progesterone FPA assay, and results were recorded in Delta mP units. Delta mP was calculated using formula:

$$\text{delta } mP = \text{Average Negative Control } mP \text{ value} - \text{Sample } mP \text{ value}$$

The testing procedure was as follows:

1. Prepare ready-to-use progesterone tracer in 80% DMSO, 20% 0.01 M PBS pH 7.3 with fluorescence intensity around 108,000 RFU on a SENTRY® (Ellie LLC, Waukesha, WI) 200 instrument;
2. Prepare ready-to-use anti-progesterone antibodies in a dilution of 1:130 (volume:volume) in 0.01 M PBS pH 7.3 containing riboflavin binding protein at a concentration of 28.5 mg/ml;

20. Read blank;
21. Add 10 µl of progesterone tracer in all tubes containing controls and samples;
22. Mix well;
23. Incubate for 15 minutes;
24. Read progesterone tracer and obtain mP values;
25. Calculate delta mP values.

Results are shown in FIGS. 6-10. The detected levels of progesterone were capable of accurately characterizing the estrous cycles of the non-pregnant cows.

Benefit of Non-Aqueous Solvent in Maintaining Progesterone in Milk Serum During Milk Clarification The importance of the presence of a non-aqueous solvent such as ethanol in maintaining progesterone in milk serum during milk clarification was tested. Milk samples from pregnant cows were clarified as described above with and without ethanol, and the resulting milk serum was tested for the presence of progesterone. The pregnancy of each cow was confirmed by veterinarian examination. Results are shown in Table 5.

TABLE 5

| | | | | FPA Without Ethanol (mP) | FPA With Ethanol (mP) | ΔmP Without Ethanol | ΔmP With Ethanol | RIA milk (ng/ml) |
|---|---|---|---|---|---|---|---|---|
| Cows | Date of Insemination | Date of Sampling | Negative Control (mP) | | | | | |
| 1 | Jun. 18, 2017 | Nov. 23, 2019 | 285.7 | 275.92 | 230.83 | 9.78 | 45.09 | 32.76 |
| 2 | Apr. 26, 2017 | Nov. 23, 2020 | 285.7 | 276.10 | 238.80 | 9.60 | 37.30 | 18.89 |
| 3 | Sep. 20, 2017 | Nov. 23, 2022 | 285.7 | 280.19 | 242.29 | 5.51 | 41.43 | 29.27 |
| 4 | Jul. 16, 2017 | Nov. 23, 2023 | 285.7 | 276.98 | 235.55 | 8.72 | 37.91 | 21.69 |
| 5 | Aug. 26, 2017 | Nov. 23, 2026 | 285.7 | 279.52 | 241.03 | 6.18 | 38.49 | 30.22 |

FPA detection of progesterone with and without ethanol.

3. Prepare control diluent by mixing one part of solvent used in extraction (99.9% alcohol) and 9 parts of sample diluent (1 M Tris buffer pH 7.7 with 0.1% EDTA);
4. Mix small part of samples being tested for use as negative control;
5. Transfer 1.5 ml of milk as negative control into three microcentrifuge tubes;
6. Transfer 1 ml of milk samples into microcentrifuge tubes;
7. Add 500 µl of solvent (99.9% alcohol) in the microcentrifuge tubes with the samples;
8. Add 60 µl of ClearMilk Buffer in all tubes containing controls and samples;
9. Mix well;
10. Incubate for 10 minutes at room temperature;
11. Incubate for 15 minutes at +4° C.;
12. Centrifuge controls and samples at 10,000×g for 5 minutes;
13. Mix 400 µl of samples and controls and 1000 µl of 1M Tris buffer pH 7.7 with 0.1% EDTA in the new microcentrifuge tube;
14. Incubate samples and control in a light treatment chamber for 30 minutes;
15. Centrifuge samples and controls in a microcentrifuge at 10,000×g for 5 minutes;
16. Transfer 1 ml of supernatant into borosilicate glass tubes;
17. Add 10 µl of antibodies in all tubes containing controls and samples;
18. Mix well;
19. Incubate for 5 minutes at room temperature;

As seen in Table 5, the samples lacking ethanol during preparation show similar results to the negative control, indicating that the progesterone did not partition with the milk serum during clarification in these samples. The radioimmunoassay (RIA) results confirm that progesterone was originally present in the milk samples. Thus, ethanol or other non-aqueous solvent is important for maintaining progesterone in the milk serum for downstream detection thereof.

Effect of Incubation Time and Temperature During Milk Coagulation

The purpose of this experiment was to compare two casein coagulation protocols for the progesterone FPA assay. The differences between the two protocols included incubation time and temperature after adding ClearMilk Buffer.

Two milk samples were used in this experiment. Sample No. 1 originated from a cow in estrus. The estrus status of the cow was confirmed by field veterinarian clinical examination. Sample No. 2 originated from a pregnant cow. The pregnancy status of the cow was confirmed by field veterinarian clinical examination.

Coagulation Protocol 1

1. Mix samples well before processing;
2. Add 1.5 ml of milk sample into four microcentrifuge tubes as controls;
3. Add 1 ml of milk sample into a microcentrifuge tube as sample;
4. Add 0.5 ml of absolute ethanol into the sample tube;
5. Mix well;
6. Add 40 µl of ClearMilk Buffer into all control and sample tubes;
7. Mix well immediately;
8. Incubate for 15 minutes at 2-8° C.;

9. Centrifuge for 5 minutes at 10,000×g (13,000 rpm);
10. Milk will separate into three layers:
    Lipid layer on the top;
    Milk serum in the middle;
    Casein at the bottom;
11. Use milk serum for FPA analysis.

Coagulation Protocol 2
1. Mix samples well before processing;
2. Add 1.5 ml of milk sample into four microcentrifuge tubes as controls;
3. Add 1 ml of milk sample into a microcentrifuge tube as sample;
4. Add 0.5 ml of absolute ethanol into the sample tube;
5. Mix well;
6. Add 40 μl of ClearMilk Buffer into all control and sample tubes;
7. Mix well immediately;
8. Incubate for 5 minutes at room temperature;
9. Centrifuge for 5 minutes at 10,000×g (13,000 rpm);
10. Milk will separate into three layers:
    Lipid layer on the top;
    Milk serum in the middle;
    Casein at the bottom;
11. Use milk serum for FPA analysis.

FPA Analysis—the Testing Procedure was the Same for Both Sample Treatment Protocols:
1. Carefully pipette 300 μl of control and sample milk serum into test tubes;
2. Add 700 μl of Sample Diluent into all control and sample tubes;
3. Use first three control tubes as negative controls;
4. Add 10 μl of 1 μg/ml progesterone solution into the fourth control tube as a positive control;
5. Mix well all tubes containing controls and samples;
6. Add 10 μl of anti-progesterone antibodies (1:130 (vol:vol)) in 0.01 M PBS pH 7.3 containing riboflavin binding protein at a concentration of 28.5 mg/ml into all tubes containing samples and controls;
7. Mix well;
8. Incubate 5 minutes at room temperature;
9. Obtain blank readings of samples and controls;
10. Add 10 μl of progesterone tracer (ready-to-use progesterone tracer in 80% DMSO, 20% 0.01 M PBS pH 7.3 with fluorescence intensity around 108,000 RFU on a SENTRY® (Ellie LLC, Waukesha, WI) 200 instrument) into all tubes containing samples and controls;
11. Mix well;
12. Incubate for 5 minutes at room temperature;
13. Obtain mP readings of all samples and controls;
14. Calculate delta mP values.
Results are shown in Table 6.

TABLE 6

FPA detection of progesterone (PG) with
different sample treatment protocols.

| Samples | PG FPA Assay result (Delta mP value) | |
| --- | --- | --- |
| | Coagulation Protocol 1 | Coagulation Protocol 2 |
| Sample No. 1 (Cow in estrus) | 8 | 6 |
| Sample No. 2 (Pregnant cow) | 47 | 41 |

Similar experiments were performed in which samples were treated according to Coagulation Protocol 2 but except for being incubated for only 1 minute after adding ClearMilk Buffer and mixing. Progesterone FPA results were similar to those outlined above with a 5-minute incubation time.

These experiments show that extended incubation times around 4° C. are not necessary and incubation times as short as 1-5 minutes at room temperature are acceptable.

Centrifugation Versus Filtration of Coagulated Milk

The purpose of this experiment was to compare centrifugation and filtration for milk clarification.

Two milk samples were used in this experiment. Sample No. 1 originated from a cow in estrus. The estrus status of the cow was confirmed by field veterinarian clinical examination. Sample No. 2 originated from a pregnant cow. The pregnancy status of the cow was confirmed by field veterinarian clinical examination.

Sample Preparation Using Centrifugation
1. Mix samples well before processing;
2. Add 1 ml of milk sample into a microcentrifuge tube;
3. Add 0.5 ml of absolute ethanol into the sample tube;
4. Mix well;
5. Add 40 ul of ClearMilk Buffer into the sample tube;
6. Mix well immediately;
7. Incubate for 5 minutes at room temperature;
8. Centrifuge for 5 minutes at 10,000×g (13,000 rpm);
9. Milk will be separated into three layers:
    Lipid layer on the top;
    Milk serum in the middle;
    Casein at the bottom;
10. Use milk serum for FPA analysis.

Sample Preparation Using Filtration
1. Mix samples well before processing;
2. Put a small amount of cotton wool in a 20-ml lock syringe, and press it to the bottom;
3. Add 3 ml of milk serum into the syringe as sample;
4. Add 1.5 ml of absolute ethanol into the syringe containing the sample and shake vigorously;
5. Add 5 drops of ClearMilk Buffer into the syringe containing the sample and gently shake;
6. Leave the syringe in the upright position at room temperature for milk to clot (5-15 minutes);
7. Mount a 0.22-μm, 25-mm polyethersulfone syringe filters on the syringe;
8. Push milk through the syringe and filter and obtain clear milk serum.

FPA Analysis—the Testing Procedure was the Same for Both Sample Treatment Protocols:
1. Carefully pipette 300 μl of milk serum samples into test tubes;
2. Add 700 μl of Sample Diluent into all sample tubes;
3. Mix well all sample tubes;
4. Add 10 μl of anti-progesterone antibodies (1:130 (vol:vol)) in 0.01 M PBS pH 7.3 containing riboflavin binding protein at a concentration of 28.5 mg/ml into all tubes containing samples;
5. Mix well;
6. Incubate 5 minutes at room temperature;
7. Obtain blank readings of samples;
8. Add 10 μl of progesterone tracer (ready-to-use progesterone tracer in 80% DMSO, 20% 0.01 M PBS pH 7.3 with fluorescence intensity around 108,000 RFU on a SENTRY® (Ellie LLC, Waukesha, WI) 200 instrument) into all tubes containing samples and controls;
9. Mix well;
10. Incubate for 5 minutes at room temperature;
11. Obtain mP readings of all samples;
12. Calculate delta mP values.
Results are shown in Table 7.

TABLE 7

FPA detection of progesterone (PG) in milk serum prepared with
centrifugation versus milk serum prepared with filtration.

|  | Sample No. 1 - Cow in Estrus (mP value) | Sample No. 2 - Pregnant Cow (mP value) | Difference between samples |
| --- | --- | --- | --- |
| Centrifugation | 278 | 242 | 36 |
| Filtration | 272 | 240 | 33 |

Similar experiments were performed with 0.1-μm, 0.45-μm, 0.7-μm, and combination 0.45/0.22-μm filters, and all types of filtration were shown to be acceptable. Use of a 0.7-μm filer is preferred to avoid excessive resistance with the syringe plunger during filtration. The filtration sufficiently removed coagulated casein and lipid from the sample while maintaining the progesterone in the sample in order to detect the progesterone in the sample using FPA.

These experiments show that that filtration can be used in place of centrifugation in preparing the milk serum for FPA.

Example 3: Reduction of Background Fluorescence Using RBP in Detection of Antibodies to *Brucella abortus*

Background

This example shows that RBP can reduce background fluorescence with FPA to determine the presence of antibodies in individual or bulk milk samples against species of the genus *Brucella*, including those that produce smooth colonies (*B. melitensis, B. abortus* and *B. suis*—Rev. sci. tech., OIE 1982). The presence of antibodies is indicative of current or recent infection with *Brucella*.

The exemplary diagnostic test described herein uses as a tracer an O-polysaccharide (OPS) extracted from *Brucella abortus* bacteria conjugated with fluorescein. See Nielsen et al. 1996; Nielsen et al. 2000; and Nielsen et al. 2001. A fluorescence polarization instrument is used to measure the polarization state of the light emitted by the OPS conjugate. When no antibodies are present, the polarization is low. Polarization increases when antibodies bind to the tracer.

Exemplary FPA *Brucella* Antibody Detection Kit

An exemplary FPA *Brucella* antibody detection kit is as follows:

| Kit Size | 250 Tests | 1000 Tests |
| --- | --- | --- |
| Negative Control | 5 ml | 20 ml |
| Positive Control | 1 ml | 2 ml |
| Sample Diluent | 250 ml | 1000 ml |
| Tracer | 3.75 ml | 15 ml |
| ClearMilk Buffer | 30 ml | 60 ml |

The Negative Control is riboflavin binding protein dissolved in 0.01 M PBS pH 7.2. The Positive Control is polyclonal anti-*Brucella abortus* antibody serum (RAB1003) from APHA Scientific (New Haw, Addlestone, Surrey, UK). The Sample Diluent is 1M Tris pH 7.7 with 0.1% (v/v) EDTA. The Tracer is *Brucella abortus* OPS-Fluorescein Conjugate. The ClearMilk Buffer is phosphate buffered saline (PBS) pH 5.8 with 750 IMCU/ml *Rhizomucor mihei* rennet. All components may contain sodium azide in an amount less than 0.1%.

Materials in addition to those in the exemplary kits for detecting *Brucella* antibodies using FPA include: an FP instrument, 10×75 mm borosilicate glass test tubes, a microcentrifuge capable of reaching 10,000×g, 1.5-ml microcentrifuge tubes, a vortex, pipettors and pipette tips, and distilled or deionized water.

Polarization readings are affected by temperature. All reagents used in the test should be at the same temperature as samples tested. It is advisable to bring all reagents and samples to room temperature.

Methods of Using Exemplary FPA *Brucella* Antibody Detection Kit for RBP Treatment and FPA Detection of *Brucella* Antibodies An exemplary RBP treatment method using the above-mentioned materials for detecting *Brucella* antibodies in milk with a SENTRY® (Ellie LLC, Waukesha, WI) 200 instrument using FPA is described below.

Delipidate Milk Samples:

There are two ways of delipidating milk samples:
1. Add 2×1.5 ml of the same milk sample into two microcentrifuge tubes and run 5 minutes at around 10,000×g. The lipid layer will be separated on the top. Collect carefully the layer below the lipid surface.
2. Add 10-50 ml of milk into the syringe and leave it vertically overnight. The lipids will separate on the top. Eject the skim milk from the syringe.

Clarify Samples:
1. Add 1 ml of skim milk sample into two separate microcentrifuge tubes;
2. Add 60 μl of ClearMilk Buffer and mix gently by rocking the tubes;
3. Incubate for 10 minutes at room temperature until milk starts to clump;
4. Slowly add 300 μl of Sample Diluent over the top of the clot in each microcentrifuge tube;
5. Centrifuge for 10 minutes in the microcentrifuge at 10,000×g.

Prepare Controls:
1. Pipette 1 ml of Sample Diluent into four test tubes and add 1 ml of DI or distilled water into each tube;
2. Use the first three tubes as negative controls;
3. Add 40 μl of Positive Control into the fourth tube and mix well.

Run the Test:
1. Pipette 1 ml of milk serum from two microcentrifuge tubes into the test tube for a total of 2 ml volume;
2. Add 20 μl of Negative Control (RBP dissolved at a concentration of 85 mg/ml in 0.01 M PBS pH 7.2) into all tubes containing control and samples;
3. Mix well;
4. Incubate 5 minutes at room temperature;
5. Obtain blank readings of controls and samples;
6. Add 15 μl of Tracer into all tubes containing control and samples;
7. Mix well;
8. Incubate 30 minutes at room temperature;
9. Obtain mP readings of controls and samples.

Test Validation:

The Negative Control should read between 70 and 90 mP. The Positive Control should read between 120 and 250 mP. In case the Negative Control is outside the range, adjust the instrument to read mean Negative Control at 80±5 mP. Depending on the instrument, this can be done without retesting samples.

Results & Interpretation:

Calculate ΔmP values for each sample by subtracting mean Negative Control mP from Sample mP.

$$\Delta mP = (\text{Sample } mP - \text{Average Negative Control } mP)$$

Test results are interpreted according to the following parameters:

Bulk Milk Samples:

| Negative | Positive |
|----------|----------|
| ≤10 | >10 |

Individual Milk Samples:

| Negative | Positive |
|----------|----------|
| ≤40 | >40 |

Methods of Using Exemplary FPA *Brucella* Antibody Detection Kit for Light Treatment and FPA Detection of *Brucella* Antibodies An exemplary light treatment method using the above-mentioned materials for detecting *Brucella* antibodies in milk with a SENTRY® (Ellie LLC, Waukesha, WI) 200 instrument using FPA is described below.

Delipidate Milk Samples:

There are two ways of delipidating milk samples:
1. Add 2 ml of milk into microcentrifuge tube and run 5 minutes at around 10,000×g. The lipid layer will be separated on the top. Collect carefully the layer below the lipid surface.
2. Add 5-50 ml of milk into the syringe and leave it vertically overnight. The lipids will separate on the top. Eject the skim milk from the syringe.

Clarify Samples:
1. Add 1.5 ml of skim milk samples into microcentrifuge tubes;
2. Add 60 μl of ClearMilk Buffer and mix gently by rocking the tube;
3. Incubate for 10 minutes at room temperature until milk starts to clump;
4. Centrifuge for 5 minutes in a microcentrifuge at 10,000×g;
5. Milk will separate into three layers:
   Lipid layer on the top;
   Milk serum in the middle;
   Casein at the bottom;
6. Pipette 1 ml of milk serum in the new micro-centrifuge tube, add 300 μl of Sample Diluent, mix well and place it in a rack of a light treatment chamber;
7. Incubate for 45 minutes;
8. Centrifuge tubes at 10,000×g for 5 minutes;
9. Transfer tubes in a rack and wait the samples to stabilize at room temperature for 30 minutes;
10. Carefully pipette 1 ml of supernatant into borosilicate glass tube.

Prepare Controls:
1. Pipette 500 μl of Sample Diluent into four test tubes and add 500 μl of DI or distilled water into each tube;
2. Use the first three tubes as negative controls;
3. Add 40 μl of Positive Control into the fourth tube and mix well;
4. Incubate for 5 minutes at room temperature.

Run the Test:
1. Obtain blank readings of controls and samples;
2. Add 10 μl of Tracer into all tubes containing control and samples;
3. Mix well;
4. Incubate 3-5 minutes at room temperature;

5. Obtain mP readings of controls and samples.

Detection of *Brucella abortus* Antibodies in RBP-Treated and Non-Treated Milk Serum Samples Using FPA The following results show that RBP treatment of milk samples can reduce background fluorescence in milk samples to detect *Brucella* antibodies using FPA.

A preliminary study was first performed to determine the effect of RBP on background fluorescence. We measured blank fluorescence of non-treated milk serum and milk serum treated with RBP to remove the background of riboflavin. In the case of non-treated sample, we only used 20 μl of sample diluted in a buffer. We used this amount in the non-treated sample because fluorescence intensity when 1 ml was used was over 1,000,000 RFU (relative fluorescence units), which can cause over-reading in the instrument. The reading with the 20 μl of non-treated sample was 125,067 RFUs for parallel fluorescence. In treated sample, by contrast, we used a full volume of 1 ml of milk serum combined with 850 μg RBP. The fluorescence intensity in this case was only 59,138 RFUs for parallel fluorescence. This reduction in background fluorescence with RBP treatment means we can increase analyte concentration in the reaction 100-fold compared to samples not treated with RBP. This greatly influences not only the sensitivity of the assay but also specificity and consistency.

We next performed a sensitivity test with milk serum treated with RBP versus milk serum not treated with RBP. We used FPA to test for *Brucella abortus* antibodies in milk serum samples treated with 850 μg RBP per 1 ml of milk serum (B1004 samples) and those not treated with RBP (B1001 samples). Only 20 μl of milk serum was used in the B1001 samples, versus 1 ml of milk serum in the B1004 samples. Samples were spiked with different amounts of rabbit polyclonal anti-*Brucella abortus* antibody serum (RAB1003). This serum is used as a standard for evaluating milk testing kits for bulk milk testing for USDA programs. Results in shown in Tables 8 and 9.

TABLE 8

FPA results for milk serum samples not treated with RBP.

| B1001 | V Blank | H Blank | V Fluor | H Fluor | mP | Delta mP |
|-------|---------|---------|---------|---------|----|----------|
| NC | 31674 | 13899 | 188568 | 150013 | 85 | |
| NC | 34453 | 15149 | 194467 | 154334 | 84 | |
| NC | 33971 | 14839 | 195894 | 155913 | 83 | |
| PC | 62547 | 27249 | 216175 | 142488 | 157 | 73 |
| RAB 1:5 | 132491 | 119447 | 286885 | 230530 | 177 | 93 |
| RAB 1:10 | 139581 | 127627 | 294768 | 249465 | 134 | 50 |
| RAB 1:50 | 139041 | 128655 | 283569 | 251065 | 97 | 13 |
| RAB 1:100 | 139695 | 129227 | 287286 | 255453 | 92 | 8 |
| RAB 1:200 | 136644 | 126457 | 286656 | 255586 | 89 | 5 |
| RAB 1:300 | 141643 | 131360 | 275708 | 246805 | 89 | 5 |

TABLE 9

FPA results for milk serum samples treated with RBP.

| B1004 | V Blank | H Blank | V Fluor | H Fluor | mP | Delta mP |
|-------|---------|---------|---------|---------|----|----------|
| NC | 9962 | 4894 | 194732 | 161725 | 96 | |
| NC | 9753 | 4984 | 192002 | 159593 | 96 | |
| NC | 10015 | 4998 | 187314 | 155298 | 97 | |
| PC | 103007 | 45113 | 268458 | 166483 | 168 | 71 |
| Neg milk | 61345 | 46702 | 216673 | 178632 | 96 | −1 |
| RAB 1:300 | 67051 | 49581 | 228007 | 179751 | 120 | 24 |
| RAB 1:400 | 65983 | 48958 | 227121 | 180812 | 114 | 18 |
| RAB 1:500 | 64175 | 47725 | 225590 | 179703 | 114 | 18 |
| RAB 1:600 | 63957 | 47951 | 222508 | 179074 | 109 | 13 |

TABLE 9-continued

FPA results for milk serum samples treated with RBP.

| B1004 | V Blank | H Blank | V Fluor | H Fluor | mP | Delta mP |
|---|---|---|---|---|---|---|
| RAB 1:700 | 63517 | 47486 | 217622 | 175596 | 106 | 10 |
| RAB 1:800 | 63991 | 47755 | 220265 | 177703 | 106 | 10 |
| RAB 1:900 | 62971 | 47324 | 213580 | 172984 | 104 | 8 |
| RAB 1:1000 | 63418 | 47087 | 217829 | 176434 | 102 | 6 |

As seen in Table 9, using a cut off value of 10 delta mP, a dilution of 1:600 comfortably reaches positive status with the B1004 samples, compared with only a 1:50 dilution with the B1001 samples (delta mP=Sample mP−Average NC mP).

We next performed a sensitivity test with milk serum treated with RBP. Table 10 shows results of multiday FPA testing on three batches (Batches 1-3) of negative milk samples. One milliliter of milk serum was used in each test. The variation between samples was minimal and no false positives were detected. We also performed the same test using 2 ml of milk serum. This showed similar results in specificity and increased sensitivity.

TABLE 10

FPB analysis on milk serum lacking *Brucella* antibodies.

| | V Blank | H Blank | V Fluor | H Fluor | mP | Delta mP |
|---|---|---|---|---|---|---|
| | | | Batch 1 | | | |
| NC | 10165 | 4998 | 121089 | 98536 | 99.1 | |
| NC | 10524 | 5314 | 123535 | 100385 | 100.3 | |
| NC | 10268 | 5168 | 123076 | 100307 | 99.0 | |
| PC | 117403 | 51363 | 218107 | 124232 | 174.2 | 75 |
| Sample 1 | 45777 | 28448 | 141922 | 109233 | 100.9 | 2 |
| Sample 2 | 45043 | 27915 | 142651 | 110188 | 99.3 | 0 |
| Sample 3 | 37478 | 21861 | 139767 | 107096 | 105.0 | 6 |
| Sample 4 | 64846 | 33950 | 166472 | 121851 | 86.5 | −13 |
| Sample 5 | 57087 | 33753 | 155036 | 116983 | 95.3 | −4 |
| Sample 6 | 42517 | 23624 | 139953 | 105039 | 103.6 | 4 |
| Sample 7 | 47607 | 26602 | 146531 | 109507 | 102.2 | 3 |
| Sample 8 | 46052 | 29050 | 143878 | 110699 | 104.2 | 5 |
| Sample 9 | 45746 | 27380 | 146576 | 112340 | 99.5 | 0 |
| Sample 10 | 48229 | 28985 | 147142 | 112149 | 100.6 | 1 |
| Sample 11 | 48003 | 30885 | 145683 | 113156 | 99.7 | 0 |
| Sample 12 | 42468 | 24790 | 140740 | 107005 | 103.0 | 4 |
| Sample 13 | 47263 | 28695 | 147669 | 112529 | 104.0 | 5 |
| Sample 14 | 46563 | 26875 | 145666 | 110504 | 98.8 | −1 |
| Sample 15 | 45380 | 27713 | 143710 | 110768 | 98.3 | −1 |
| Sample 16 | 46218 | 28393 | 145278 | 111893 | 99.3 | 0 |
| Sample 17 | 50305 | 28913 | 148115 | 111196 | 100.3 | 1 |
| Sample 18 | 46461 | 28869 | 144965 | 111711 | 100.4 | 1 |
| Sample 19 | 45853 | 27911 | 145092 | 110767 | 104.0 | 5 |
| Sample 20 | 46180 | 28161 | 141785 | 108192 | 102.7 | 3 |
| | | | Batch 2 | | | |
| NC | 10146 | 5078 | 123310 | 100934 | 96.9 | |
| NC | 10100 | 4976 | 128917 | 105893 | 95.6 | |
| NC | 9952 | 4956 | 124400 | 101809 | 97.4 | |
| PC | 99348 | 43616 | 200414 | 117623 | 168.4 | 72 |
| Sample 21 | 49398 | 31321 | 148221 | 114880 | 97.8 | 1 |
| Sample 22 | 48637 | 28330 | 147697 | 112487 | 95.4 | −1 |
| Sample 23 | 48501 | 29571 | 146682 | 112974 | 95.5 | −1 |
| Sample 24 | 58485 | 39076 | 155117 | 120356 | 100.4 | 4 |
| Sample 25 | 69737 | 51499 | 168513 | 134682 | 99.8 | 3 |
| Sample 26 | 39336 | 22181 | 139588 | 107473 | 94.7 | −2 |
| Sample 27 | 49348 | 30283 | 146601 | 112543 | 97.6 | 1 |
| Sample 28 | 51453 | 31079 | 149949 | 114534 | 96.8 | 0 |
| Sample 29 | 48736 | 29862 | 147442 | 113356 | 97.6 | 1 |
| Sample 30 | 43936 | 25677 | 142648 | 109321 | 96.7 | 0 |
| Sample 31 | 53333 | 33191 | 150755 | 115731 | 96.8 | 0 |
| Sample 32 | 58185 | 36847 | 155067 | 118923 | 96.8 | 0 |
| Sample 33 | 47779 | 30120 | 144584 | 111995 | 97.6 | 1 |
| Sample 34 | 51947 | 31991 | 147850 | 112967 | 98.5 | 2 |

TABLE 10-continued

FPB analysis on milk serum lacking *Brucella* antibodies.

| | V Blank | H Blank | V Fluor | H Fluor | mP | Delta mP |
|---|---|---|---|---|---|---|
| Sample 35 | 51215 | 33484 | 150539 | 117332 | 98.6 | 2 |
| Sample 36 | 49379 | 28470 | 146068 | 110710 | 94.8 | −2 |
| Sample 37 | 49923 | 29637 | 147804 | 112438 | 97.5 | 1 |
| Sample 38 | 60645 | 41616 | 158131 | 123933 | 98.4 | 2 |
| | | | Batch 3 | | | |
| NC | 9972 | 4890 | 126885 | 104098 | 96.0 | |
| NC | 10125 | 4913 | 127564 | 103806 | 99.8 | |
| NC | 10082 | 5007 | 125728 | 102996 | 96.7 | |
| PC | 111343 | 48840 | 209231 | 119728 | 173.8 | 76 |
| Sample 39 | 57103 | 36660 | 155277 | 119623 | 98.1 | 1 |
| Sample 40 | 49841 | 30771 | 145640 | 111827 | 97.4 | 0 |
| Sample 41 | 52592 | 31674 | 149574 | 113733 | 97.4 | 0 |
| Sample 42 | 48886 | 29162 | 143714 | 109478 | 96.9 | −1 |
| Sample 43 | 48830 | 28331 | 145107 | 109894 | 96.8 | −1 |
| Sample 44 | 52568 | 30507 | 150382 | 113402 | 96.6 | −1 |
| Sample 45 | 54304 | 32136 | 150071 | 113464 | 95.6 | −2 |
| Sample 46 | 47587 | 28556 | 144317 | 110100 | 99.3 | 2 |
| Sample 47 | 50170 | 28291 | 145445 | 109236 | 95.4 | −2 |
| Sample 48 | 49690 | 28467 | 147515 | 111426 | 96.3 | −1 |
| Sample 49 | 69143 | 49183 | 164571 | 130237 | 95.5 | −2 |
| Sample 50 | 54096 | 35428 | 150422 | 117167 | 96.0 | −2 |
| Sample 51 | 51114 | 32926 | 148278 | 115189 | 97.1 | 0 |
| Sample 52 | 45178 | 26821 | 141345 | 108448 | 95.9 | −2 |
| Sample 53 | 48967 | 29540 | 146970 | 112808 | 95.4 | −2 |
| Sample 54 | 46554 | 26265 | 143753 | 108601 | 96.9 | −1 |
| Sample 55 | 37119 | 21741 | 136448 | 106038 | 95.9 | −2 |
| Sample 56 | 38540 | 21981 | 138419 | 106441 | 97.7 | 0 |
| Sample 57 | 53931 | 34314 | 150395 | 116055 | 96.7 | −1 |
| Sample 58 | 62024 | 41709 | 155906 | 121439 | 95.6 | −2 |
| Sample 59 | 59701 | 36628 | 152876 | 115731 | 95.8 | −2 |
| Sample 60 | 50135 | 28909 | 149446 | 113375 | 94.9 | −3 |
| Sample 61 | 42251 | 26215 | 141779 | 110617 | 96.3 | −1 |
| Sample 62 | 49589 | 33171 | 147312 | 116024 | 96.4 | −1 |
| Sample 63 | 58784 | 40795 | 155803 | 122916 | 97.2 | 0 |
| Sample 64 | 46360 | 28287 | 142597 | 109801 | 96.9 | −1 |
| Sample 65 | 49438 | 29428 | 148019 | 113003 | 96.5 | −1 |
| Sample 66 | 54142 | 36511 | 150005 | 117844 | 96.1 | −1 |
| Sample 67 | 71234 | 53054 | 166315 | 133178 | 99.4 | 2 |
| Sample 68 | 62865 | 41274 | 156331 | 120893 | 94.1 | −3 |
| Sample 69 | 47130 | 27758 | 145911 | 111570 | 96.1 | −1 |
| Sample 70 | 42359 | 25546 | 139556 | 107721 | 97.8 | 0 |
| Sample 71 | 55031 | 32667 | 152854 | 116094 | 93.5 | −4 |
| Sample 72 | 50277 | 29944 | 147905 | 112781 | 96.0 | −1 |
| Sample 73 | 45131 | 25874 | 142743 | 108769 | 95.6 | −2 |
| Sample 74 | 67608 | 38552 | 165123 | 121652 | 93.9 | −4 |
| Sample 75 | 45677 | 26815 | 143600 | 109215 | 100.2 | 3 |
| Sample 76 | 48553 | 30039 | 144068 | 110493 | 99.7 | 2 |
| Sample 77 | 48491 | 28422 | 145486 | 109665 | 102.4 | 5 |
| Sample 78 | 57348 | 36299 | 150441 | 114838 | 98.9 | 1 |
| Sample 79 | 49150 | 33425 | 142658 | 112092 | 100.3 | 3 |
| Sample 80 | 42874 | 27494 | 139871 | 108974 | 101.0 | 3 |
| Sample 81 | 46701 | 28940 | 145103 | 112110 | 98.0 | 0 |
| Sample 82 | 53675 | 34418 | 150031 | 115696 | 99.0 | 1 |
| Sample 83 | 45906 | 29677 | 143872 | 112271 | 99.2 | 2 |

Example 4: Detecting *Brucella* Antigen in RBP-Treated Samples Using FPA

Background

It is often needed to detect *Brucella* antigens in milk of suspect cows, sheep, goats etc. Milk is the best sample as *Brucella* is found in milk, but not in serum. In the present example, we spiked milk with killed *Brucella* cells then tested the milk for *Brucella* antigens using FPA.

Procedure

1. Add killed *Brucella* bacteria in milk samples in final concentrations 1 mg/ml, 100 μg/ml, 10 μg/ml, and 1 μg/ml;

2. Transfer 1 ml of spiked milk samples plus one negative sample (as a negative control) into 1.5 ml microcentrifuge tubes;
3. Add 60 µl of ClearMilk Buffer PBS pH 5.8 with 750 IMCU/ml *Rhizomucor mihei* rennet and mix well;
4. Incubate around 10 minutes until milk starts to clump;
5. Add 300 µl of 1 M Tris pH 7.7 with 0.1% EDTA on the top of milk clot.
6. Centrifuge the sample at around 10,000×g for 5 minutes in a microcentrifuge;
7. Transfer 1 ml of the milk serum from samples into borosilicate glass tubes;
8. Add 20 µl of *Brucella* Positive Control serum (rabbit polyclonal anti-*Brucella abortus* antibody serum (RAB) from the *Brucella* Reference Unit (Liverpool, UK)) into all tubes containing controls and samples;
9. Add 10 µl of riboflavin binding protein (RBP) (85 mg/ml) into all tubes containing controls and samples;
10. Mix well;
11. Incubate 5 minutes;
12. Read blank;
13. Add 10 µl of *Brucella* Tracer (*Brucella abortus* OPS-fluorescein conjugate) into all tubes containing controls and samples;
14. Mix well;
15. Incubate 3-5 minutes;
16. Obtain mP values;
17. Calculate delta mP values (delta mP=negative control mP–spiked sample mP).

Results

As seen in Table 11, we were able to detect down to 10 µg/ml of *Brucella* in milk samples.

TABLE 11

Detection of *B. abortus* antigen.

|  | delta mP* | Results |
| --- | --- | --- |
| 1 mg/ml *B. abortus* in milk | 59 | POS |
| 100 ug/ml *B. abortus* in milk | 35 | POS |
| 10 ug/ml *B. abortus* in milk | 10 | POS |
| 1 ug/ml of *B. abortus* in milk | 0 | NEG |

*delta mP = Average PC in Negative Milk mP – Spiked Milk mP

REFERENCES

Hamazume Y, Mega T, Ikenaka T. Characterization of hen egg white- and yolk-riboflavin binding proteins and amino acid sequence of egg white-riboflavin binding protein. *J Biochem.* 1984 June; 95(6):1633-44.

Hong J Y, Choi M J. Development of one-step fluorescence polarization immunoassay for progesterone. *Biol Pharm Bull.* 2002 October; 25(10):1258-62.

Murthy U S, Podder S K, Adiga P R. The interaction of riboflavin with a protein isolated from hen's egg white: a spectrofluorimetric study. *Biochim Biophys Acta.* 1976 May 20; 434(1):69-81.

Nielsen K, Gall D, Jolley M, Leishman G, Balsevicius S, Smith P, Nicoletti P, Thomas F. A homogeneous fluorescence polarization assay for detection of antibody to *Brucella abortus.* J Immunol Methods. 1996 Sep. 9; 195(1-2):161-8.

Nielsen K, Gall D. Fluorescence polarization assay for the diagnosis of brucellosis: a review. J Immunoassay Immunochem. 2001; 22(3):183-201.

Nielsen K, Lin M, Gall D, Jolley M. Fluorescence polarization immunoassay: detection of antibody to *Brucella abortus.* Methods. 2000 September; 22(1):71-6.

Nishikimi M, Kyogoku Y. Flavin-protein interaction in egg white flavoprotein. *J Biochem.* 1973 June; 73(6):1233-42.

Varriale A, Pennacchio A, Pinto G, Oliviero G, D'Errico S, Majoli A, Scala A, Capo A, Pennacchio A, Di Giovanni S, Staiano M, D'Auria S. A Fluorescence Polarization Assay To Detect Steroid Hormone Traces in Milk. *J Agric Food Chem.* 2015 Oct. 21; 63(41):9159-64.

Wu et al. X F, Cai Z X, Sun S G, Huang Q, Ren G D, He L, Ma M H. [Investigation of interaction between riboflavin and riboflavin binding protein by fluorescence spectroscopy]. *Guang Pu Xue Yu Guang Pu Fen Xi.* 2012 March; 32(3):719-22.

Zandomeneghi M, Carbonaro L, Zandomeneghi G. Biochemical fluorometric method for the determination of riboflavin in milk. *J Agric Food Chem.* 2007 Jul. 25; 55(15):5990-4.

What is claimed is:

1. A method of treating and testing a sample, the method comprising:
   treating the sample to reduce riboflavin-dependent autofluorescence in the sample, wherein the treating comprises adding riboflavin binding protein to the sample, irradiating the sample, or a combination thereof;
   clarifying the sample while maintaining the analyte in the sample, wherein the sample comprises a milk product and the analyte is a hydrophobic analyte, wherein the clarifying comprises adding a non-aqueous polar solvent to the sample, coagulating casein in the sample, and, after adding the non-aqueous polar solvent to the sample, removing the coagulated casein from the sample, wherein the non-aqueous polar solvent is added to the sample in an amount sufficient to maintain the analyte in the sample;
   adding a tracer to the sample; and
   detecting fluorescence from the tracer in the sample, wherein the detected fluorescence indicates an amount of the analyte in the sample.

2. The method of claim 1, wherein the treating comprises adding riboflavin binding protein to the sample.

3. The method of claim 2, wherein the detecting is performed in the presence of the riboflavin binding protein added to the sample.

4. The method of claim 1, wherein the clarifying further comprises removing lipid from the sample.

5. The method of claim 1, wherein the non-aqueous polar solvent comprises an alcohol.

6. The method of claim 1, wherein the non-aqueous polar solvent comprises ethanol.

7. The method of claim 1, wherein the non-aqueous polar solvent is added to the sample at a final concentration of from 10% v/v to 50% v/v.

8. The method of claim 1, wherein the analyte has an average solubility less than 100 µg/ml in distilled water at room temperature.

9. The method of claim 1, wherein the analyte is a steroid hormone.

10. The method of claim 1, wherein the coagulating comprises digesting casein in the sample with a rennet to coagulate the casein.

11. The method of claim 10, wherein the digesting is conducted in the presence of the non-aqueous polar solvent.

12. The method of claim 10, wherein the non-aqueous polar solvent comprises an alcohol and the digesting is conducted in the presence of the non-aqueous polar solvent at a concentration in the sample of from 10% v/v to 50% v/v.

13. The method of claim 12, wherein the non-aqueous polar solvent comprises ethanol.

14. The method of claim 12, wherein the clarifying further comprises removing lipid from the sample.

15. The method of claim 12, wherein the analyte has an average solubility less than 100 g/ml in distilled water at room temperature.

16. The method of claim 12, wherein the analyte is a steroid hormone.

17. The method of claim 12, wherein:

the non-aqueous polar solvent comprises ethanol;

the clarifying further comprises removing lipid from the sample; and the analyte has an average solubility less than 100 μg/ml in distilled water at room temperature.

18. The method of claim 17, wherein the treating comprises adding riboflavin binding protein to the sample.

19. The method of claim 12, wherein:

the non-aqueous polar solvent comprises ethanol;

the clarifying further comprises removing lipid from the sample; and the analyte is a steroid hormone.

20. The method of claim 19, wherein the treating comprises adding riboflavin binding protein to the sample.

* * * * *